United States Patent
Tetsuka et al.

(10) Patent No.: US 11,272,605 B2
(45) Date of Patent: Mar. 8, 2022

(54) X-RAY DIAGNOSTIC APPARATUS, AND X-RAY TUBE

(71) Applicant: CANON MEDICAL SYSTEMS CORPORATION, Otawara (JP)

(72) Inventors: Akio Tetsuka, Shioyagun (JP); Yuki Totsuka, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/601,865

(22) Filed: Oct. 15, 2019

(65) Prior Publication Data

US 2020/0146135 A1 May 7, 2020

(30) Foreign Application Priority Data

Oct. 15, 2018 (JP) .............................. JP2018-194441

(51) Int. Cl.
*H05G 1/08* (2006.01)
*H05G 1/56* (2006.01)

(52) U.S. Cl.
CPC .............. *H05G 1/085* (2013.01); *H05G 1/56* (2013.01)

(58) Field of Classification Search
None
See application file for complete search history.

(56) References Cited

U.S. PATENT DOCUMENTS

2010/0183117 A1* 7/2010 Tsumuraya ............. H01J 35/26
378/9

FOREIGN PATENT DOCUMENTS

JP 2014-7085 A 1/2014
WO WO 2009/011422 A1 1/2009

* cited by examiner

*Primary Examiner* — Hoon K Song
(74) *Attorney, Agent, or Firm* — Oblon, McClelland, Maier & Neustadt, L.L.P.

(57) ABSTRACT

An X-ray diagnostic apparatus according to an embodiment includes: an X-ray tube including a target configured to generate X-rays in response to emission of electrons thereto, a plurality of filaments configured to emit electrons into substantially the same position on the target, and a grid used in common among the plurality of filaments; intermediate potential setting circuitry configured to set intermediate potential in a position between the plurality of filaments and the target by using the grid; and filament potential controlling circuitry configured to change one or more filaments selected from among the plurality of filaments to emit the electrons to the target, by controlling potential levels of the plurality of filaments with respect to the intermediate potential for each filament, in conjunction with switching of X-ray tube voltage.

12 Claims, 12 Drawing Sheets

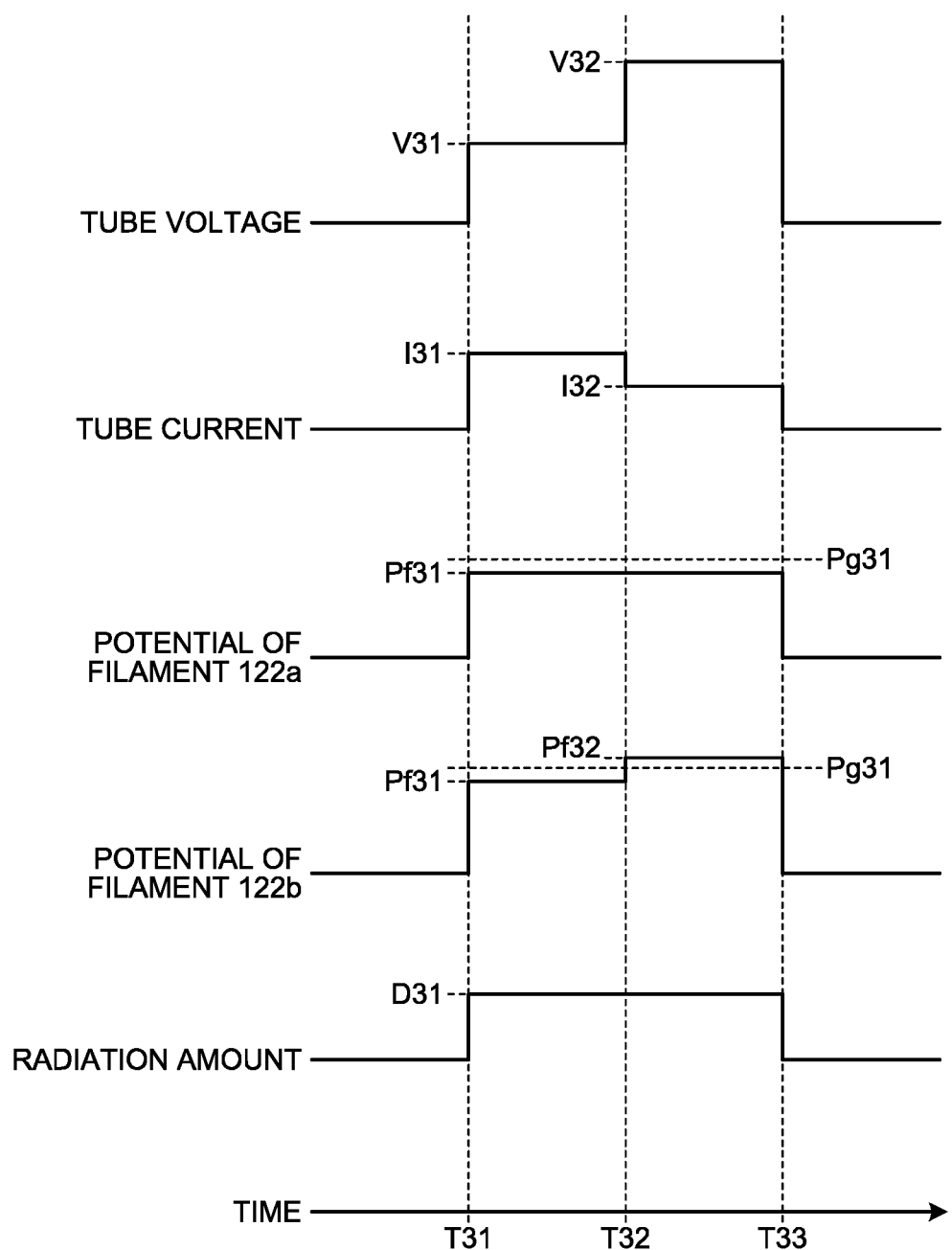

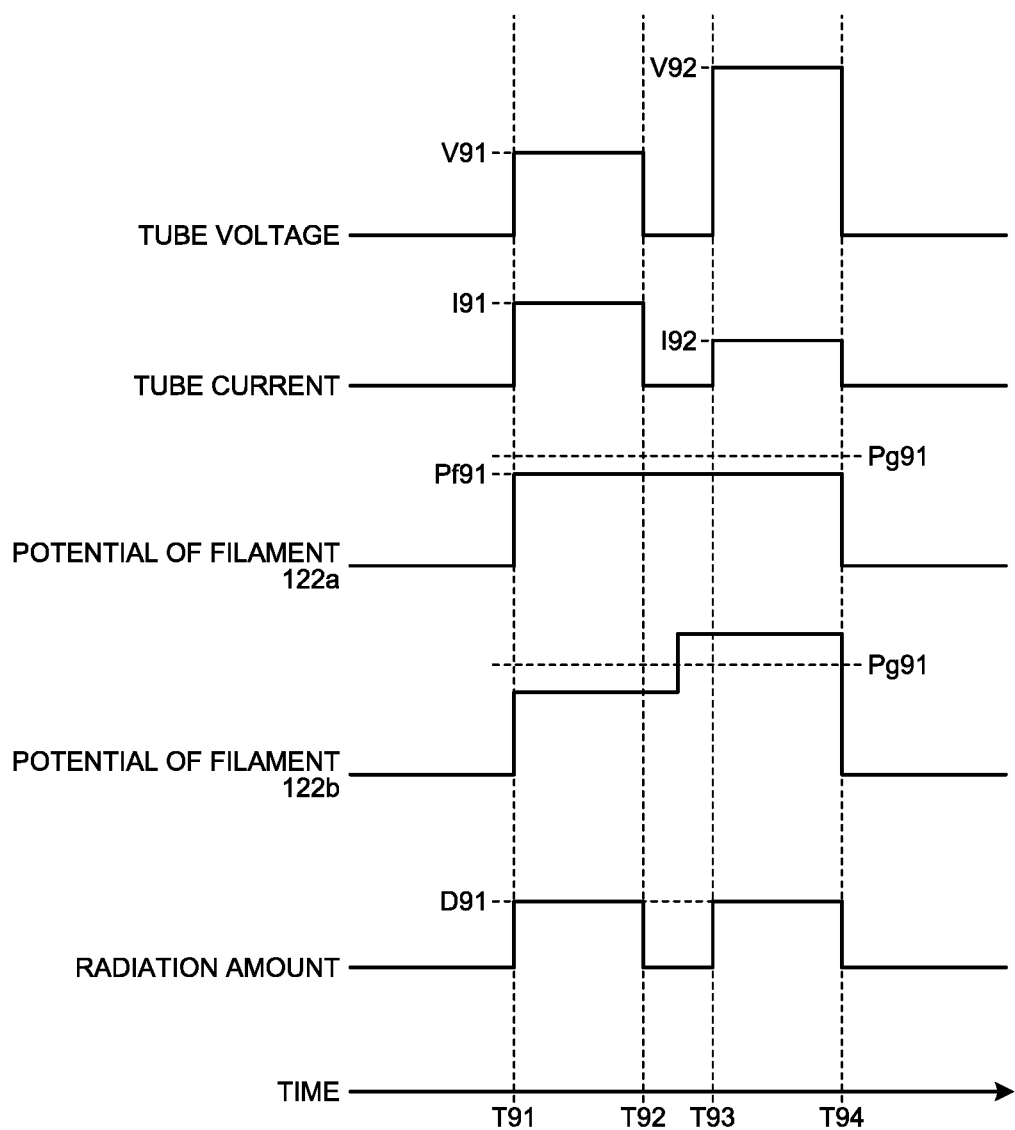

X-RAY DIAGNOSTIC APPARATUS, AND X-RAY TUBE

CROSS-REFERENCE TO RELATED APPLICATIONS

This application is based upon and claims the benefit of priority from Japanese Patent Application No. 2018-194441, filed on Oct. 15, 2018; the entire contents of which are incorporated herein by reference.

FIELD

Embodiments described herein relate generally to an X-ray diagnostic apparatus and an X-ray tube.

BACKGROUND

A technique is known by which X-ray image data corresponding to different levels of energy is acquired while varying energy of X-rays so as to discriminate substances contained in an examined subject by using the notion that different substances have different X-ray absorption characteristics. In this situation, the energy of the X-rays is varied by switching X-ray tube voltage (hereinafter, "tube voltage") to be supplied to an X-ray tube.

BRIEF DESCRIPTION OF THE DRAWINGS

FIG. 6 is a chart illustrating yet another example of the dual-energy acquisition according to the first embodiment;

FIG. 12 is a chart illustrating an example of a dual-energy acquisition according to a third embodiment.

DETAILED DESCRIPTION

An X-ray diagnostic apparatus includes an X-ray tube, intermediate potential setting circuitry, and filament potential controlling circuitry. The X-ray tube includes: a target configured to generate X-rays in response to emission of electrons thereto; a plurality of filaments configured to emit electrons into substantially the same position on the target; and a grid used in common among the plurality of filaments. The intermediate potential setting circuitry is configured to set intermediate potential in a position between the plurality of filaments and the target by using the grid. The filament potential controlling circuitry is configured to change one or more filaments selected from among the plurality of filaments to emit the electrons to the target, by controlling potential levels of the plurality of filaments with respect to the intermediate potential for each filament, in conjunction with switching of X-ray tube voltage.

Exemplary embodiments of an X-ray diagnostic apparatus will be explained in detail below, with reference to the accompanying drawings.

To begin with, a first embodiment will be explained. In the present embodiment, an X-ray diagnostic apparatus 1 including an X-ray high-voltage device 11 and an X-ray tube 12 will be explained. Further, in the present embodiment, an example of acquiring X-ray image data corresponding to two types of energy will be explained. In other words, in the present embodiment, a situation where a Dual-Energy (DE) acquisition is performed will be explained as an example.

Figure 1:
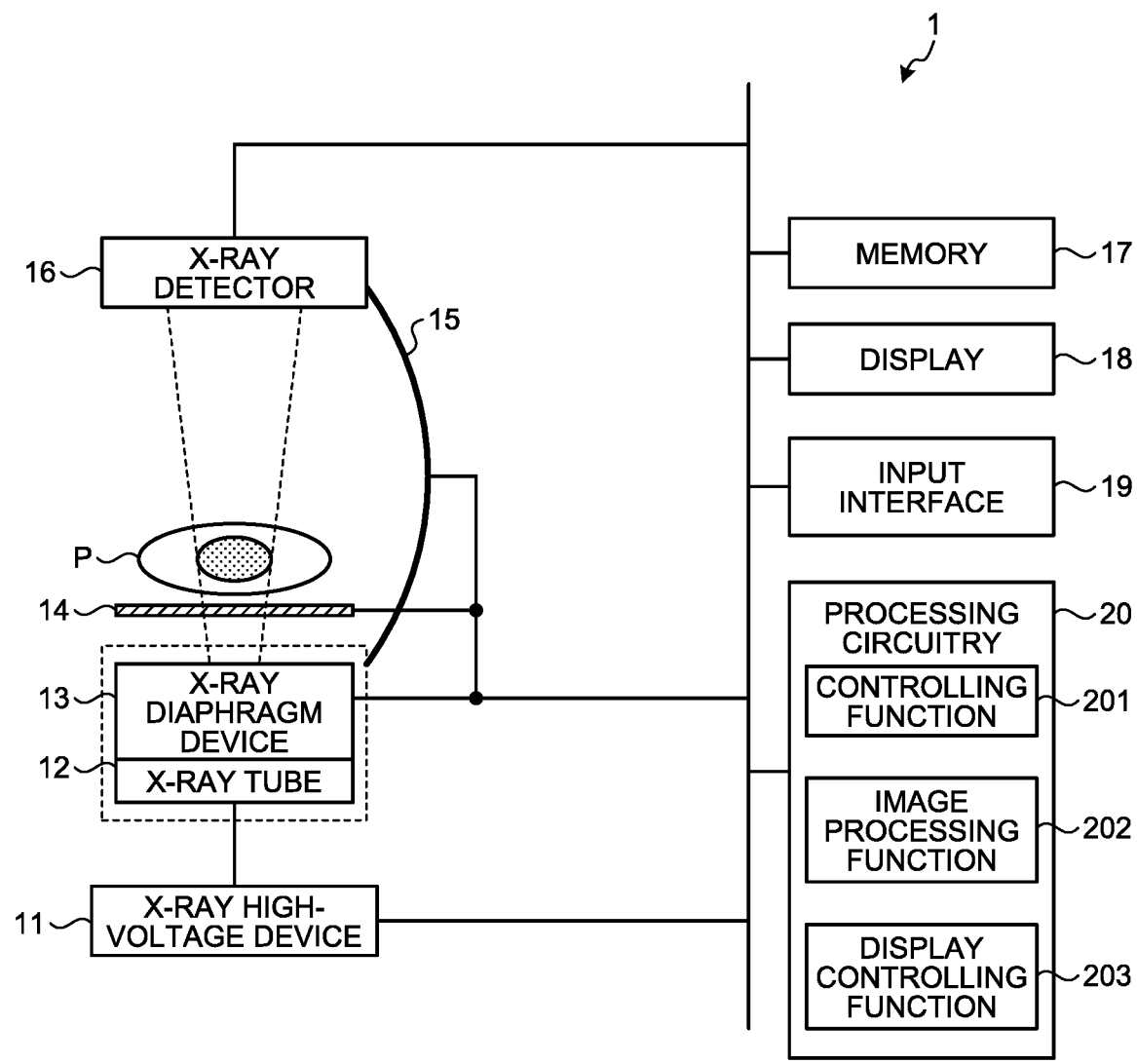
FIG. 1 is a block diagram illustrating an exemplary configuration of an X-ray diagnostic apparatus according to a first embodiment.

FIG. 1 is a block diagram illustrating an exemplary configuration of the X-ray diagnostic apparatus 1 according to the first embodiment. As illustrated in FIG. 1, the X-ray diagnostic apparatus 1 includes the X-ray high-voltage device 11, the X-ray tube 12, an X-ray diaphragm device 13, a tabletop 14, a C-arm 15, an X-ray detector 16, a memory 17, a display 18, an input interface 19, and processing circuitry 20.

The X-ray high-voltage device 11 is configured to supply high voltage to the X-ray tube 12, under control of the processing circuitry 20. For example, the X-ray high-voltage device 11 includes: a high-voltage generating device including electric circuits such as a transformer, a rectifier, and the like and being configured to generate the high voltage to be applied to the X-ray tube 12; X-ray tube voltage controlling circuitry (hereinafter, "tube voltage controlling circuitry") configured to control output voltage in accordance with the X-rays radiated by the X-ray tube 12; grid controlling circuitry configured to control a grid of the X-ray tube 12; and filament controlling circuitry configured to control a filament of the X-ray tube 12. The X-ray high-voltage device 11 will be explained later.

The X-ray tube 12 is a vacuum tube including a negative pole (a filament) configured to generate thermo electrons and a positive pole (a target) configured to generate the X-rays in response to collisions of the thermo electrons. By using the tube voltage supplied thereto from the X-ray high-voltage device 11, the X-ray tube 12 is configured to generate the X-rays by emitting the thermo electrons from the filament to the target. In this situation, the X-ray tube 12 is configured to generate the X-rays having energy corresponding to the tube voltage supplied thereto from the X-ray high-voltage device 11. The X-ray tube 12 will be explained later.

The X-ray diaphragm device 13 includes a collimator configured to narrow down the radiation range of the X-rays generated by the X-ray tube 12 and a filter configured to adjust the X-rays generated by the X-ray tube 12.

The collimator included in the X-ray diaphragm device 13 includes, for example, four diaphragm blades that are slidable. By sliding the diaphragm blades, the collimator is configured to narrow down the X-rays generated by the X-ray tube 12 before being radiated onto an examined subject (hereinafter "patient") P. In this situation, the diaphragm blades are plate-like members configured by using lead or the like and are provided in the vicinity of an X-ray radiation opening of the X-ray tube 12 to adjust the radiation range of the X-rays.

For the purpose of reducing radiation exposure for the patient P and improving the quality of X-ray image data, the filter included in the X-ray diaphragm device 13 is configured to change the radiation quality of passing X-rays with the material and/or the thickness thereof, so as to reduce a soft X-ray component that is easily absorbed by the patient P or to reduce a high-energy component that may degrade the contrast of the X-ray image data. Further, the filter is configured to attenuate the X-rays so that the X-rays radiated from the X-ray tube 12 onto the patient P have a distribution determined in advance, by changing the radiation amount and the radiation range of the X-rays with the material, the thickness, and/or the position thereof.

For example, the X-ray diaphragm device 13 includes a driving mechanism such as a motor and an actuator or the like and is configured to control the radiation of the X-rays by operating the driving mechanism, under control of the processing circuitry 20 (explained later). For example, the X-ray diaphragm device 13 is configured to control the radiation range of the X-rays to be radiated onto the patient P, by applying drive voltage to the driving mechanism in accordance with a control signal received from the processing circuitry 20 and adjusting the opening degree of the diaphragm blades of the collimator. Further, for example, the X-ray diaphragm device 13 is configured to control the distribution of radiation amounts of the X-rays to be radiated onto the patient P, by applying drive voltage to the driving mechanism in accordance with a control signal received from the processing circuitry 20 and adjusting the position of the filter.

The tabletop 14 is a bed on which the patient P is placed and is disposed over a bed driving device (not illustrated). The patient P is not included in the X-ray diagnostic apparatus 1. For example, the bed driving device includes a driving mechanism such as a motor and an actuator or the like and is configured to control moving and tilting of the tabletop 14 by operating the driving mechanism under the control of the processing circuitry 20 (explained later). For example, the bed driving device moves and tilts the tabletop 14 by applying drive voltage to the driving mechanism in accordance with a control signal received from the processing circuitry 20.

The C-arm 15 is configured to hold the X-ray tube 12 with the X-ray diaphragm device 13 and the X-ray detector 16 so as to oppose each other while the patient P is interposed therebetween. For example, the C-arm 15 includes a driving mechanism such as a motor and an actuator or the like and is configured to rotate and to move by operating the driving mechanism under the control of the processing circuitry 20 (explained later). For example, the C-arm 15 is configured to rotate/move the X-ray tube 12, the X-ray diaphragm device 13, and the X-ray detector 16 with respect to the patient P and to control the radiation position and the radiation angle of the X-rays, by applying drive voltage to the driving mechanism in accordance with a control signal received from the processing circuitry 20. Although FIG. 1 illustrates an example in which the X-ray diagnostic apparatus 1 is a single-plane apparatus, possible embodiments are not limited to this example, and the X-ray diagnostic apparatus 1 may be a bi-plane apparatus.

The X-ray detector 16 is an X-ray Flat Panel Detector (FPD) including detecting elements arranged in a matrix formation, for example. Each of the detecting elements included in the X-ray detector 16 is configured to detect X-rays radiated from the X-ray tube 12 and to store therein an electric charge corresponding to the detected X-ray amount. Further, each of the detecting elements included in the X-ray detector 16 is configured to output a detection signal based on the stored electric charge to the processing circuitry 20. In this situation, each of the detecting elements included in the X-ray detector 16 is capable of outputting the detection signal while holding the stored electric charge therein. In other words, the X-ray detector 16 is capable of performing a non-destructive reading process.

The memory 17 is realized, for example, by using a semiconductor memory element such as a Random Access Memory (RAM) or a flash memory, or a hard disk, an optical disk, or the like. For example, the memory 17 is configured to receive and store therein the X-ray image data acquired by the processing circuitry 20. Further, the memory 17 is configured to store therein computer programs (hereinafter "programs") corresponding to various types of functions executed by circuits included in the X-ray diagnostic apparatus 1. Alternatively, the memory 17 may be realized with a group of servers (a cloud) connected to the X-ray diagnostic apparatus 1 via a network.

The display 18 is configured to display various types of information. For example, the display 18 is configured to display a Graphical User Interface (GUI) used for receiving instructions from an operator and various types of X-ray images, under the control of the processing circuitry 20. For example, the display 18 may be a liquid crystal display device or a Cathode Ray Tube (CRT) display device. The display 18 may be of a desktop type or may be configured by using a tablet terminal or the like capable of wirelessly communicating with the processing circuitry 20.

The input interface 19 is configured to receive various types of input operations from the operator, to convert the received input operations into electrical signals, and to output the electrical signals to the processing circuitry 20. For example, the input interface 19 may be realized by using a mouse, a keyboard, a trackball, a switch, a button, a joystick, a touchpad on which an input operation can be performed by touching the operation surface thereof, a touch screen in which a display screen and a touchpad are integrally formed, a contactless input circuit using an optical sensor, an audio input circuit, and/or the like. The input interface 19 may be configured by using a tablet terminal or the like capable of wirelessly communicating with the processing circuitry 20. Further, the input interface 19 does not necessarily have to include one or more physical operation component parts such as a mouse and a keyboard. For instance, possible examples of the input interface 19 include an electric signal processing circuit configured to receive an electric signal corresponding to an input operation from an external input device provided separately from the X-ray diagnostic apparatus 1 and to output the electric signal to the processing circuitry 20.

The processing circuitry 20 is configured to control operations of the entirety of the X-ray diagnostic apparatus 1, by executing a controlling function 201, an image processing function 202, and a display controlling function 203. For example, by reading and executing a program corresponding to the controlling function 201 from the memory 17, the processing circuitry 20 is configured to control various types of functions of the processing circuitry 20 on the basis of input operations received from the operator via the input interface 19.

Further, the controlling function 201 is configured to perform an image taking process on the patient P, by controlling operations of an image taking system including the X-ray high-voltage device 11, the X-ray tube 12, the X-ray diaphragm device 13, the tabletop 14, the C-arm 15, and the X-ray detector 16. For example, the controlling function 201 is configured to rotate and move the C-arm 15, by controlling operations of the C-arm 15. Further, the controlling function 201 is configured to move and tilt the tabletop 14, by controlling operations of the couch driving device.

Further, the controlling function 201 is configured to control the radiation of the X-rays onto the patient P, by controlling operations of the X-ray high-voltage device 11. For example, the controlling function 201 is configured to cause X-rays having high energy and X-rays having low energy to be radiated onto the patient P, by switching the tube voltage to be supplied to the X-ray tube 12 by controlling operations of the X-ray high-voltage device 11. Further, the controlling function 201 is configured to narrow down the radiation range of the X-rays generated by the X-ray tube 12, by adjusting the opening degree of the diaphragm blades included in the collimator by controlling operations of the X-ray diaphragm device 13. Also, the controlling function 201 is configured to control the distribution of radiation amounts of the X-rays, by adjusting the position of the filter by controlling operations of the X-ray diaphragm device 13. Furthermore, the controlling function 201 is configured to receive the detection signals output from the X-ray detector 16.

Further, by reading and executing a program corresponding to the image processing function 202 from the memory 17, the processing circuitry 20 is configured to generate the X-ray image data on the basis of the detection signals output from the X-ray detector 16 and to store the generated X-ray image data into the memory 17. In other words, the image processing function 202 is configured to generate the X-ray image data based on a detection result obtained by the X-ray detector 16. Further, the image processing function 202 may process the generated X-ray image data. For example, the image processing function 202 may perform a noise reducing process or a scattered ray correcting process by using image processing filters on the X-ray image data.

Further, the image processing function 202 is configured to perform a process (hereinafter, "discriminating process") related to discriminating substances contained in the patient P, on the basis of the generated X-ray image data. For example, by performing the discriminating process, the image processing function 202 discriminates the types, the atomic numbers, the density levels, and the like of the substances contained in the patient P. In one example, the image processing function 202 is configured to calculate the difference between X-ray image data based on detection signals acquired by using the X-rays having high energy and X-ray image data based on detection signals acquired by using the X-rays having low energy. With this arrangement, the image processing function 202 is able to generate image data corresponding to each substance contained in the patient P. For example, because X-ray absorption characteristics are different between bones and soft tissues, the image processing function 202 is able to generate image data representing the bones and image data representing the soft tissues. In other words, as the discriminating process, the image processing function 202 is configured to perform a process of generating a plurality of pieces of image data separated on the basis of the differences in the X-ray absorption characteristics. In other words, the image processing function 202 is configured to separate the bones and the soft tissues from each other rendered in the generated X-ray image data.

In the following sections, the X-ray image data based on the detection signals acquired by using the X-rays having high energy will be referred to as a high-energy image. Further, in the following sections, the X-ray image data based on the detection signals acquired by using the X-rays having low energy will be referred to as a low-energy image. For example, the image processing function 202 is configured to generate the image data corresponding to each substance contained in the patient P, by calculating the difference between the high-energy image and the low-energy image.

In another example, the image processing function 202 is configured to perform the discriminating process by using a trained model provided with a function to perform the discriminating process. For example, the image processing function 202 inputs, to a machine learning engine, the high-energy image and the low-energy image as input-side data, and the image data representing the bones and the image data representing the soft tissues as output-side data. Subsequently, the machine learning engine learns a relationship between the input-side data and the output-side data. For example, the machine-learning engine learns the relationship between the input-side data and the output-side data, by using any of various types of algorithms such as deep learning, a neural network, a logistic regression analysis, a non-linear discriminant analysis, a Support Vector Machine (SVM), a random forest, and Naive Bayes. As a result, the image processing function 202 generates a trained model M1 provided with a function to generate the image data representing the bones and the image data representing the soft tissues, on the basis of the high-energy image and the low-energy image. Further, by inputting a high-energy image and a low-energy image to the trained model M1, the image processing function 202 is able to cause the trained model M1 to generate image data representing bones and image data representing sort tissues. In other words, the image processing function 202 is configured to perform the process of generating the plurality of pieces of image data separated on the basis of the differences in the X-ray absorption characteristics, as a discriminating process using the trained model M1.

Further, for example, the image processing function 202 inputs, to the machine learning engine, the high-energy image and the low-energy image as input-side data and information indicating substances as output-side data. In this situation, the information indicating the substances may be, for example, information indicating the substances represented by pixels in the high-energy image or the low-energy image. In one example, the information indicating the substances may be label information (e.g., a label indicating the bones, a label indicating the soft tissues) appended to the pixels in the high-energy image or the low-energy image by an image interpreting doctor or a medical technologist. Subsequently, the machine learning engine learns a relationship between the input-side data and the output-side data. As a result, the image processing function 202 generates a trained model M2 provided with a function to output information indicating the substances represented by the pixels in the high-energy image or the low-energy image, on the basis of the high-energy image and the low-energy image. Further, by inputting a high-energy image and a low-energy image to the trained model M2, the image processing function 202 is able to cause the trained model M2 to output information indicating the substances. For example, the image processing function 202 causes the trained model M2 to output image data in which label information is appended to the pixels in the high-energy image or the low-energy image.

Although the example was explained in which the image processing function 202 generates the trained models, possible embodiments are not limited to this example. In other words, the trained model may be generated by another apparatus different from the X-ray diagnostic apparatus 1.

Further, by reading and executing a program corresponding to the display controlling function 203 from the memory 17, the processing circuitry 20 is configured to cause the display 18 to display various types of images. For example, the display controlling function 203 is configured to cause the display 18 to display a GUI used for receiving instructions from the operator, the X-ray image data generated on the basis of the detection signals, and image data (e.g., the image data representing the bones and the image data representing the soft tissues) resulting from the discriminating process. Further, the controlling function 201 is configured to control data transmission and reception between the X-ray diagnostic apparatus 1 and other apparatuses and devices. For example, the controlling function 201 transmits various types of image data to an image storage device (not illustrated).

Figure 2:
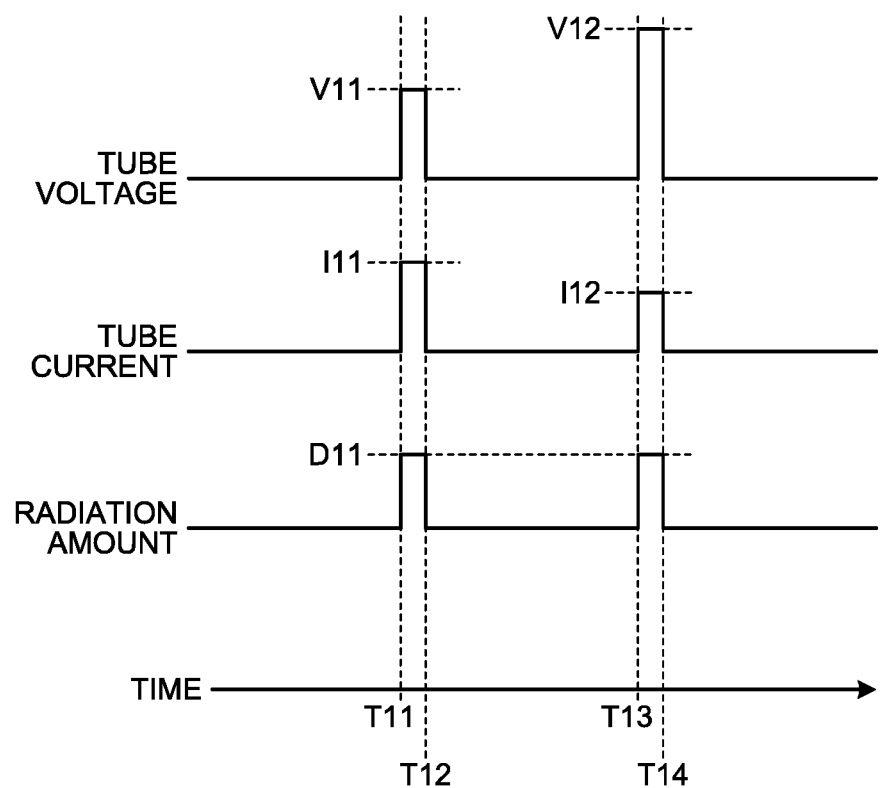
FIG. 2 is a chart illustrating an example of a dual-energy acquisition according to the first embodiment.

Next, an example of a dual-energy acquisition realized by switching tube voltage will be explained with reference to FIG. 2. FIG. 2 is a chart illustrating an example of the dual-energy acquisition according to the first embodiment. FIG. 2 illustrates an example in which the tube voltage is switched between tube voltage V11 and tube voltage V12. The tube voltage V11 corresponds to X-rays having low energy. In contrast, the tube voltage V12 is voltage higher than the tube voltage V11 and corresponds to X-rays having high energy.

At first, the X-ray high-voltage device 11 applies heat to the filament of the X-ray tube 12 by causing an electric current to flow therein. The electric current caused to flow in the filament for the purpose of applying heat thereto will hereinafter be referred to as a "filament current". Subsequently, in the time period from the time T11 to the time T12, the X-ray high-voltage device 11 supplies the tube voltage V11 to the X-ray tube 12. As a result, the X-ray tube 12 radiates an X-ray pulse having low energy onto the patient P, in the time period from the time T11 to the time T12.

In this situation, in the time period from the time T11 to the time T12, a tube current I11 flowing in the X-ray tube 12 has a value corresponding to the temperature of the filament and the tube voltage V11. In this situation, because the tube current I11 has a value corresponding to the number of thermo electrons released from the target, the tube current I11 is, in principle, dependent on the temperature of the filament. However, the tube current I11 is also dependent on the tube voltage V11 because the higher the tube voltage V11 is, the larger is the force that pulls electrons out of the target. Further, the radiation amount (or dose) D11 of the X-rays radiated onto the patient P in the time period from the time T11 to the time T12 has a value proportional to the product of the tube voltage V11 and the tube current I11.

Further, in the time period from the time T11 to the time T12, the X-ray detector 16 detects X-rays having passed through the patient P and having low energy. Further, at the time T12, the X-ray detector 16 reads an electric charge corresponding to the X-ray amount detected in the time period from the time T11 to the time T12 and outputs detection signals to the processing circuitry 20. Further, the image processing function 202 generates X-ray image data on the basis of the detection signals output from the X-ray detector 16. In other words, the image processing function 202 is configured to generate a low-energy image on the basis of the detection signals output from the X-ray detector 16.

Further, in the time period from the time T12 to the time T13, the X-ray high-voltage device 11 lowers the temperature of the filament. More specifically, the X-ray high-voltage device 11 lowers the temperature of the filament by decreasing the filament current on and after the time T12. Subsequently, in the time period from the time T13 to the time T14, the X-ray high-voltage device 11 supplies the tube voltage V12 to the X-ray tube 12. As a result, in the time period from the time T13 to the time T14, the X-ray tube 12 radiates an X-ray pulse having high energy onto the patient P.

In this situation, in the time period from the time T13 to the time T14, a tube current I12 flowing in the X-ray tube 12 has a value corresponding to the temperature of the filament and the tube voltage V12. Further, in the time period from the time T13 to the time T14, the radiation amount D12 of the X-rays radiated onto the patient P has a value proportional to the product of the tube voltage V12 and the tube current I12.

Accordingly, to arrange the radiation amount D11 and the radiation amount D12 to be constant, it is necessary to arrange the tube current I12 to have a smaller value than the tube current I11, as illustrated in FIG. 2. More specifically, by sufficiently lowering the temperature of the filament in the time period from the time T12 to the time T13, the X-ray high-voltage device 11 is able to maintain the radiation amount between the two sessions of the X-ray pulse radiation, by arranging the tube current I12 to be smaller than the tube current I11.

Further, in the time period from the time T13 to the time T14, the X-ray detector 16 detects X-rays having passed through the patient P and having high energy. Further, at the time T14, the X-ray detector 16 reads an electric charge corresponding to the X-ray amount detected in the time period from the time T13 to the time T14 and outputs detection signals to the processing circuitry 20. Further, the image processing function 202 generates X-ray image data on the basis of the detection signals output from the X-ray detector 16. In other words, the image processing function 202 is configured to generate a high-energy image on the basis of the detection signals output from the X-ray detector 16.

In the example illustrated in FIG. 2, the image processing function 202 performs a discriminating process on substances contained in the patient P, on the basis of the low-energy image based on the X-rays radiated in the pulse form in the time period from the time T11 to the time T12 and the high-energy image based on the X-rays radiated in the pulse form in the time period from the time T13 to the time T14. For example, by utilizing the notion that the X-ray absorption characteristics are different between the bones and the soft tissues, the image processing function 202 separates the bones and the soft tissues from each other by calculating the difference between the low-energy image and the high-energy image. Further, for example, the image processing function 202 performs the discriminating process by inputting the low-energy image and the high-energy image to the trained model.

In this situation, it may be impossible, in some situations, to perform the discriminating process when there is a positional difference between the low-energy image and the high-energy image. For example, when the patient P has movement between the two sessions of X-ray radiation (in the time period from the time T12 to the time T13), it may be impossible, in some situations, to perform the discriminating process due to a positional difference between the low-energy image and the high-energy image. In one example, when there is movement or body movement due to respiration or pulsation of the patient P between the two sessions of the X-ray radiation, it may be impossible, in some situations, to perform the discriminating process due to the positional difference between the low-energy image and the high-energy image. Consequently, in the example in FIG. 2, it is not easy to perform the discriminating process on a site (e.g., the chest) having much movement.

Figure 3:
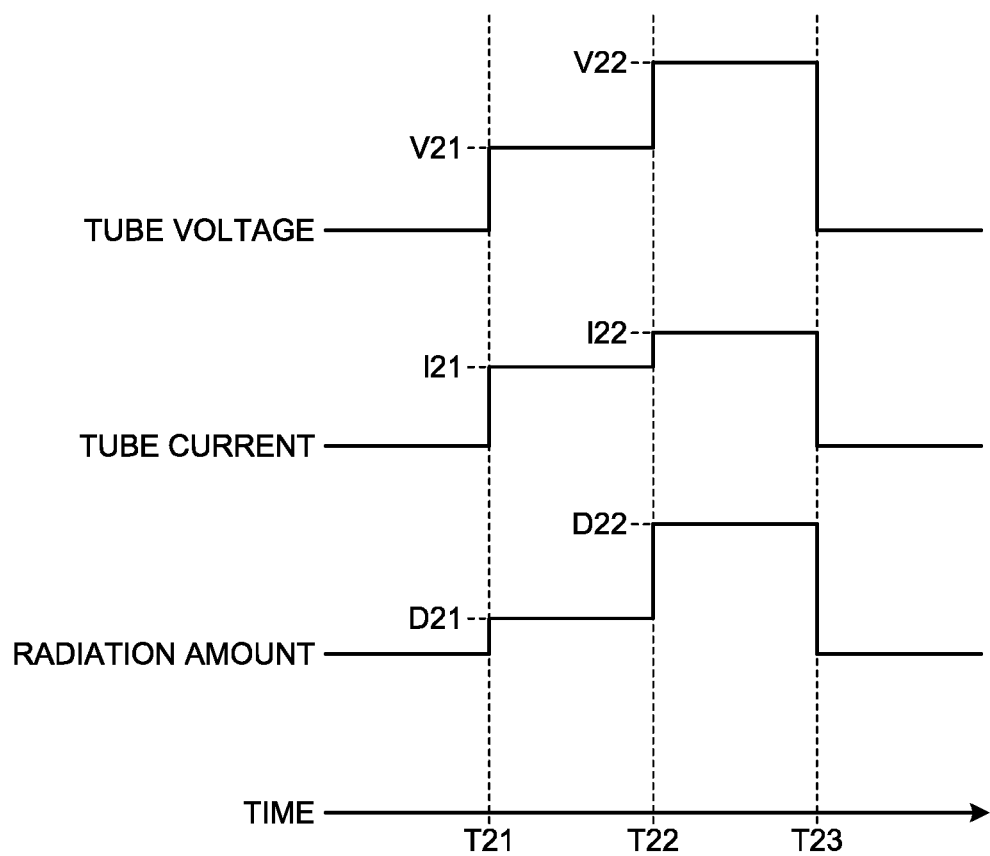
FIG. 3 is a chart illustrating another example of the dual-energy acquisition according to the first embodiment.

To prevent the positional difference between the low-energy image and the high-energy image, it may be an idea to acquire the low-energy image and the high-energy image in a short period of time. For example, as illustrated in FIG. 3, it may be an idea to acquire the low-energy image and the high-energy image during the X-ray radiation time period corresponding to one pulse, by switching the tube voltage while the X-ray pulse is being radiated. FIG. 3 is a chart illustrating the example of the dual-energy acquisition according to the first embodiment. FIG. 3 illustrates the example in which the tube voltage to be supplied to the X-ray tube 12 is switched between the tube voltage V21 and the tube voltage V22. The tube voltage V21 corresponds to X-rays having low energy. In contrast, the tube voltage V22 is voltage higher than the tube voltage V21 and corresponds to X-rays having high energy.

At first, the X-ray high-voltage device 11 applies heat to the filament of the X-ray tube 12 by using a filament current. Subsequently, in the time period from the time T21 to the time T22, the X-ray high-voltage device 11 supplies the tube voltage V21 to the X-ray tube 12. In this situation, in the time period from the time T21 to the time T22, a tube current I21 flowing in the X-ray tube 12 has a value corresponding to the temperature of the filament and the tube voltage V21. Further, in the time period from the time T21 to the time T22, the radiation amount D21 of the X-rays radiated onto the patient P has a value proportional to the product of the tube voltage V21 and the tube current I21.

Further, in the time period from the time T21 to the time T22, the X-ray detector 16 detects X-rays having passed through the patient P and having low energy. Further, at the time T22, the X-ray detector 16 reads an electric charge corresponding to the X-ray amount detected in the time period from the time T21 to the time T22 and outputs detection signals to the processing circuitry 20. In this situation, the X-ray detector 16 performs a non-destructive reading process. In other words, while holding the electric charges stored in the detecting elements, the X-ray detector 16 outputs the detection signals corresponding to the stored electric charges. Further, the image processing function 202 generates a low-energy image on the basis of the detection signals output from the X-ray detector 16.

Further, at the time T22, the X-ray high-voltage device 11 switches the tube voltage to be supplied to the X-ray tube 12 from the tube voltage V21 to the tube voltage V22. In other words, at the time T22, the X-ray high-voltage device 11 switches the tube voltage, so that the X-ray detector 16 performs a non-destructive reading process in response to the switching of the tube voltage. The non-destructive reading process performed by the X-ray detector 16 at the time T22 is an example of the first reading process. Further, in the time period from the time T22 to the time T23, the X-ray high-voltage device 11 supplies the tube voltage V22 to the X-ray tube 12. In this situation, a tube current I22 flowing in the X-ray tube 12 in the time period from the time T22 to the time T23 has a value corresponding to the temperature of the filament and the tube voltage V22. Further, the radiation amount D22 of the X-rays radiated onto the patient P in the time period from the time T22 to the time T23 has a value proportional to the product of the tube voltage V22 and the tube current I22.

Further, in the time period from the time T22 to the time T23, the X-ray detector 16 detects X-rays having passed through the patient P and having high energy. Further, at the time T23, the X-ray detector 16 reads an electric charge corresponding to the X-ray amount detected in the time period from the time T21 to the time T23 and outputs detection signals to the processing circuitry 20. The reading process performed by the X-ray detector 16 at the time T23 is an example of the second reading process. Further, the image processing function 202 calculates the difference between the detection signals output at the time T23 and the detection signals output at the time T22.

In other words, the detection signals output at the time T23 correspond to the X-ray amount detected in the time period from the time T21 to the time T23. The detection signals output at the time T22 correspond to the X-ray amount detected in the time period from the time T21 to the time T22. Accordingly, by calculating the difference between the detection signals output at the time T23 and the detection signals output at the time T22, the image processing function 202 calculates signals corresponding to the X-ray amount detected in the time period from the time T22 to the time T23. After that, the image processing function 202 generates a high-energy image on the basis of the calculated signals.

As explained above, the X-ray high-voltage device 11 switches the tube voltage while the X-ray tube 12 is radiating the X-ray pulse. As a result, the X-ray high-voltage device 11 is able to acquire the low-energy image and the high-energy image in a short period of time and to thereby prevent the positional difference between the images.

In the present example, as illustrated in FIG. 3, the radiation amount D22 in the time period from the time T22 to the time T23 has a value larger than that of the radiation amount D21 in the time period from the time T21 to the time T22. In other words, in the example in FIG. 3, the radiation amount of the X-rays changes due to the switching of the tube voltage. The reason is that the tube current I22 has a larger value than the tube current I21, in addition to that the tube voltage V22 is higher than the tube voltage V21.

Further, in the example in FIG. 3, it may be impossible, in some situations, to perform the discriminating process because the low-energy image and the high-energy image are images taken by using the mutually-different radiation amounts. In other words, because the radiation amounts of the X-rays used for the image taking processes are different, it may be impossible, in some situations, to discriminate the substances contained in the patient P, even when the difference is calculated between the low-energy image and the high image or when the low-energy image and the high-energy image are input to the trained model.

To maintain the radiation amount before and after the switching of the tube voltage, it may be an idea to arrange the tube current I22 to have a smaller value than that of the tube current I21. For example, it may be an idea to arrange the tube current I22 to have a smaller value than that of the tube current I21 by arranging the filament temperature in the time period from the time T22 to the time T23 to be lower than the filament temperature in the time period from the time T21 to the T22. However, in the example in FIG. 3, because there is not enough time to change the filament temperature, it would not be easy to control the tube currents by controlling the filament temperature.

Figure 4:
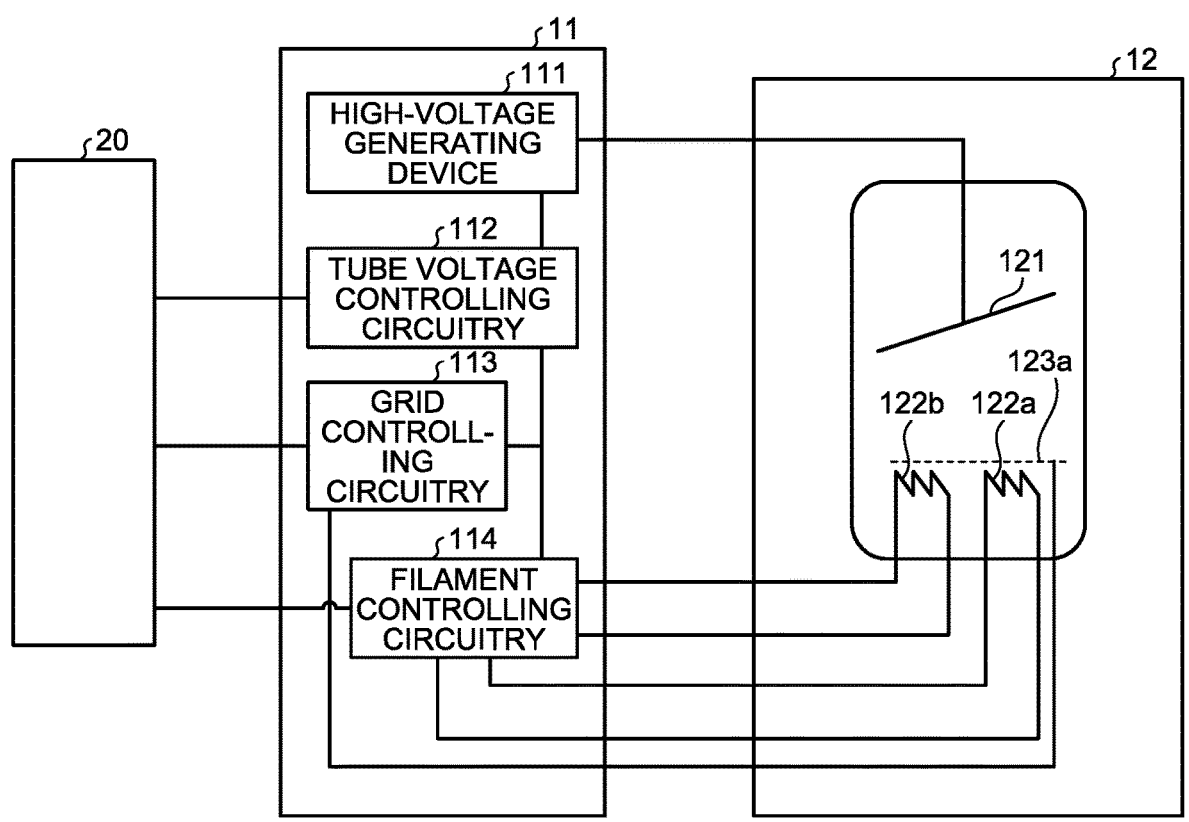
FIG. 4 is a diagram illustrating an example of the X-ray diagnostic apparatus according to the first embodiment.

To cope with this situation, the X-ray diagnostic apparatus 1 according to the first embodiment is configured to control the tube currents at the time of the switching of the tube voltage by performing the processes described in detail below. In the following sections, the X-ray diagnostic apparatus 1 will be explained in detail, with reference to FIG. 4. FIG. 4 is a diagram illustrating an example of the X-ray diagnostic apparatus 1 according to the first embodiment.

For the sake of convenience in the explanation, FIG. 4 illustrates only the processing circuitry 20, the X-ray high-voltage device 11, and the X-ray tube 12 among the constituent elements of the X-ray diagnostic apparatus 1. Within the X-ray diagnostic apparatus 1, constituent elements related to the radiation of the X-rays may collectively be referred to as an X-ray radiating device. The X-ray radiating device includes, for example, the X-ray high-voltage device 11 and the X-ray tube 12.

As illustrated in FIG. 4, the X-ray tube 12 includes a target 121, a filament 122a, a filament 122b, and a grid 123a. The target 121 is configured to generate X-rays in response to electrons emitted thereto from the filament 122a and the filament 122b. The target 121 is an example of the target.

Further, the filament 122a and the filament 122b are configured to generate the electrons to be emitted to the target 121. In this situation, the filament 122a and the filament 122b are configured to emit the electrons into substantially the same position on the target 121. In other words the filament 122a and the filament 122b have substantially the same focal point. For example, the filament 122a and the filament 122b are provided in such positions in the X-ray tube 12 that the focal point is formed in substantially the same position on the target 121. Alternatively, the X-ray tube 12 may be configured to control trajectories of the electrons emitted from the filament 122a to the target 121 and the trajectories of the electrons emitted from the filament 122b to the target 121 by controlling an electric field formed between the filaments 122a and 122b and the target 121, so that the electrons are emitted into substantially the same position on the target 121. The filament 122a and the filament 122b constitute an example of the plurality of filaments. Further, the grid 123a is used in common by the filament 122a and the filament 122b. The grid 123a is an example of the grid.

Further, as illustrated in FIG. 4, the X-ray high-voltage device 11 includes a high-voltage generating device 111, tube voltage controlling circuitry 112, grid controlling circuitry 113, and filament controlling circuitry 114. The high-voltage generating device 111 is a device configured to generate high voltage. The high-voltage generating device 111 may be of a transformer type or an inverter type. Under the control of the processing circuitry 20, the tube voltage controlling circuitry 112 is configured to control the tube voltage to be supplied to the X-ray tube 12, by controlling the high-voltage generating device 111. The tube voltage controlling circuitry 112 is an example of a first controlling unit. Further, the tube voltage controlling circuitry 112 is an example of the tube voltage controlling circuitry.

The grid controlling circuitry 113 is configured to set intermediate potential in a position between the filaments 122a and 122b and the target 121, by controlling the grid 123a under the control of the processing circuitry 20. For example, the grid 123a illustrated in FIG. 4 is a mesh made of metal and is positioned between the filaments 122a and 122b and the target 121. In this situation, by applying voltage to the grid 123a, the grid controlling circuitry 113 sets the intermediate potential in the position between the filaments 122a and 122b and the target 121. In other words, the grid controlling circuitry 113 sets the potential of the grid 123a as the intermediate potential. In this situation, the grid controlling circuitry 113 is an example of a second controlling unit. Further, the grid controlling circuitry 113 is an example of the intermediate potential setting circuitry.

Under the control of the processing circuitry 20, the filament controlling circuitry 114 is configured to change the filament(s) that emit electrons to the target 121 between the filament 122a and the filament 122b by controlling the potential levels of the filament 122a and the filament 122b with respect to the intermediate potential for each filament, in conjunction with the switching of the tube voltage. In this situation, the filament controlling circuitry 114 is an example of a third controlling unit. Further, the filament controlling circuitry 114 is an example of the filament potential controlling circuitry.

Figure 5:
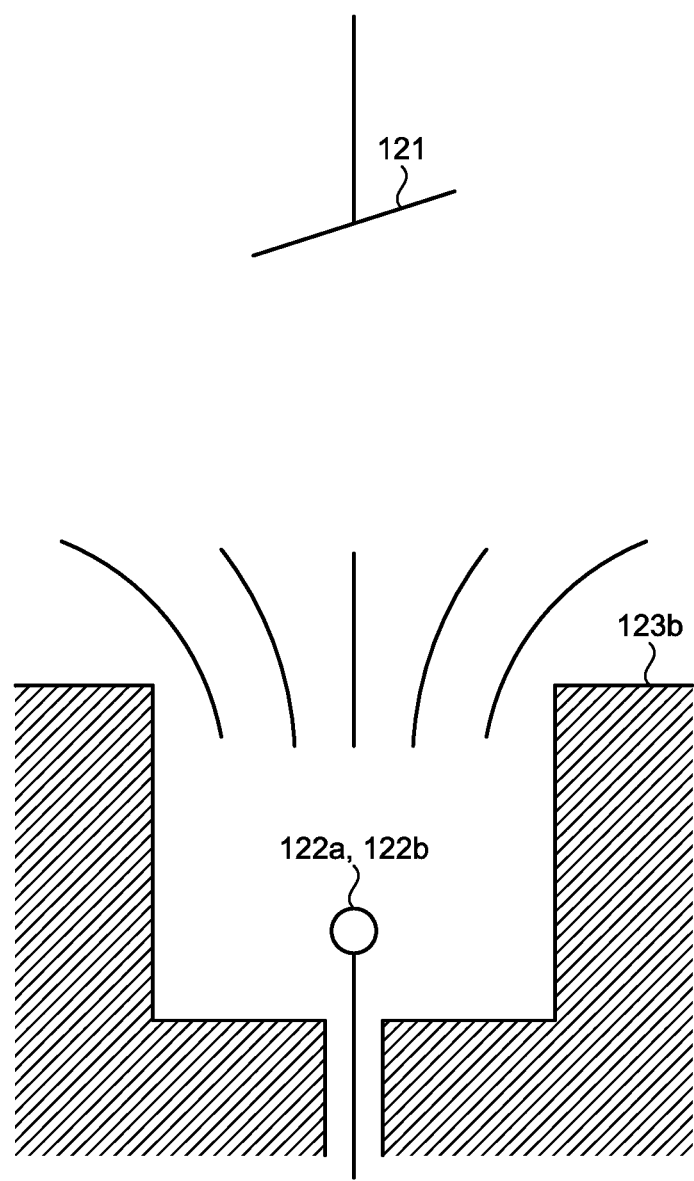
FIG. 5 is a drawing illustrating an example of a grid according to the first embodiment.

Although FIG. 4 illustrates the grid 123a as an example of the grid, possible embodiments are not limited to this example. For instance, the X-ray tube 12 may include a grid 123b illustrated in FIG. 5 in place of the grid 123a. FIG. 5 is a drawing illustrating another example of the grid according to the first embodiment.

The grid 123b illustrated in FIG. 5 has a cup-like shape covering the filament 122a and the filament 122b and has an opening toward the target 121. In this situation, the grid controlling circuitry 113 is configured to generate an electric field by applying voltage to the grid 123b. As a result, the grid controlling circuitry 113 sets intermediate potential in a position between the filaments 122a and 122b and the target 121, by controlling the potential in positions in the surroundings of the grid 123b. In the following sections, the intermediate potential set by the grid controlling circuitry 113 by using either the grid 123a or the grid 123b will be referred to as intermediate potential Pg.

The X-ray diagnostic apparatus 1 has thus been explained in detail. The X-ray diagnostic apparatus 1 structured as described above is configured to appropriately control the tube currents at the time of the switching of the tube voltage. Next, processes performed by the X-ray diagnostic apparatus 1 will be explained with reference to FIG. 6. FIG. 6 is a chart illustrating yet another example of a dual-energy acquisition according to the first embodiment.

FIG. 6 illustrates an example in which the tube voltage to be supplied to the X-ray tube 12 is switched between tube voltage V31 and tube voltage V32. The tube voltage V31 corresponds to X-rays having low energy. In contrast, the tube voltage V32 is voltage higher than the tube voltage V31 and corresponds to X-rays having high energy. The settings of the tube voltage will be explained later.

At first, the filament controlling circuitry 114 applies heat to the filament 122a and the filament 122b by using a filament current. In this situation, as illustrated in FIG. 4, the filament controlling circuitry 114 is individually connected to each of the filaments 122a and 122b. Accordingly, the filament controlling circuitry 114 is able to cause mutually-different filament currents to flow in the filament 122a and the filament 122b. The settings of the filament currents will be explained later. Further, by controlling either the grid 123a or the grid 123b, the grid controlling circuitry 113 is configured to set intermediate potential Pg31 in a position between the filaments 122a and 122b and the target 121.

Subsequently, in the time period from the time T31 to the time T32, the tube voltage controlling circuitry 112 supplies the tube voltage V31 to the X-ray tube 12. More specifically, the tube voltage controlling circuitry 112 supplies the tube voltage V31 to the X-ray tube 12, by applying voltage to the position between the filaments 122a and 122b and the target 121 by controlling the high-voltage generating device 111.

In this situation, the filament controlling circuitry 114 is configured to control the potential levels of the filament 122a and the filament 122b with respect to the intermediate potential Pg31 for each filament. More specifically, as illustrated in FIG. 6, the filament controlling circuitry 114 exercises control so that the potential of the filament 122a and the potential of the filament 122b are each equal to potential Pf31, which is lower than the intermediate potential Pg31. With this arrangement, the electrons generated from the filament 122a and the filament 122b are emitted to the target 121 without being blocked by the intermediate potential Pg31.

Figure 7A:
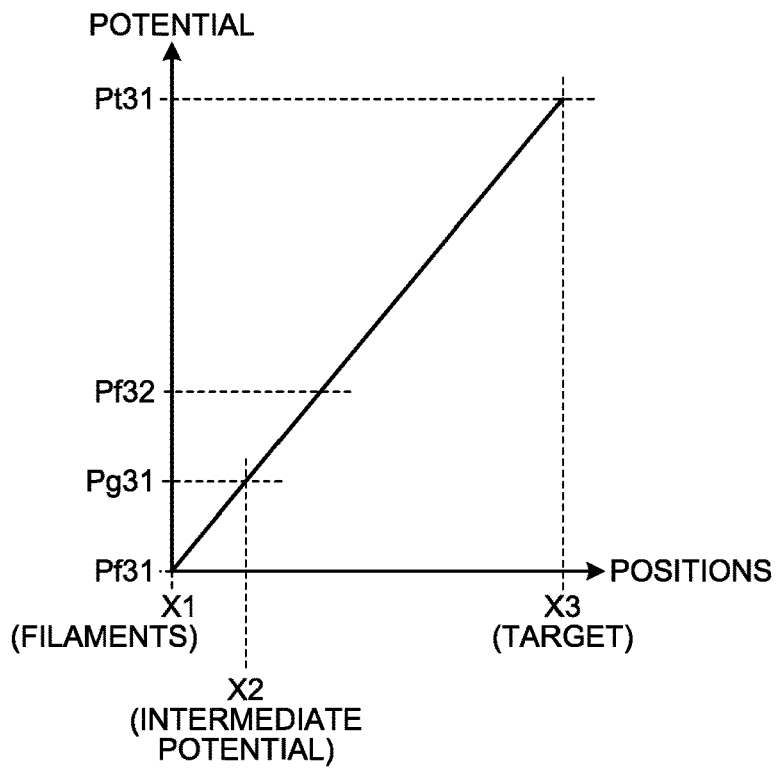
FIG. 7A is a chart for explaining control over filament potential according to the first embodiment.

Next, the potential Pf31 will be explained with reference to FIG. 7A. FIG. 7A is a chart for explaining the control over the filament potential according to the first embodiment. In FIG. 7A, the horizontal axis expresses positions, whereas the vertical axis expresses potential. As indicated on the horizontal axis in FIG. 7A, the filament 122a and the filament 122b are in a position X1. Further, the target 121 is in a position X3. In FIG. 7A, the potential of the target 121 is expressed as potential Pt31. Further, the intermediate potential Pg31 is set in a position X2, which is positioned between the position X1 and the position X3.

As illustrated in FIG. 7A, the intermediate potential Pg31 is higher than the potential Pf31. Further, the potential Pt31 of the target 121 is higher than the intermediate potential Pg31. In this situation, because the electrons generated from the filament 122a and the filament 122b have negative electric charges, the electrons move toward positions having higher potential. In other words, in the example in FIG. 7A, the electrons generated from the filament 122a and the filament 122b in the position X1 pass through the position X2 and are emitted to the target 121 in the position X3.

Returning to the description of FIG. 6, in the time period from the time T31 to the time T32, a tube current I31 flowing in the X-ray tube 12 has a value corresponding to the total number of electrons generated from the filament 122a and the filament 122b. Further, in the time period from the time T31 to the time T32, the radiation amount D31 of the X-rays radiated onto the patient P has a value proportional to the product of the tube voltage V31 and the tube current I31.

Further, in the time period from the time T31 to the time T32, the X-ray detector 16 detects X-rays having passed through the patient P and having low energy. Further, at the time T32, the X-ray detector 16 reads an electric charge corresponding to the X-ray amount detected in the time period from the time T31 and the time T32 and outputs detection signals to the processing circuitry 20. In this situation, the X-ray detector 16 performs a non-destructive reading process. Further, the image processing function 202 generates a low-energy image on the basis of the detection signals output from the X-ray detector 16.

Further, at the time T32, the tube voltage controlling circuitry 112 switches the tube voltage to be supplied to the X-ray tube 12 from the tube voltage V31 to the tube voltage V32. In other words, at the time T32, the tube voltage controlling circuitry 112 switches the tube voltage, so that the X-ray detector 16 performs a non-destructive reading process in response to the switching of the tube voltage. In this situation, the non-destructive reading process performed by the X-ray detector 16 at the time T32 is an example of the first reading process. Further, in the time period from the time T32 to the time T33, the tube voltage controlling circuitry 112 supplies the tube voltage V32 to the X-ray tube 12. In this situation, in conjunction with the switching of the tube voltage, the filament controlling circuitry 114 changes the filament(s) that emit electrons to the target 121 between the filament 122a and the filament 122b, by controlling the potential levels of the filament 122a and the filament 122b with respect to the intermediate potential Pg31 for each filament.

More specifically, as illustrated in FIG. 6, the filament controlling circuitry 114 maintains the potential of the filament 122a at the potential Pf31. In contrast, the filament controlling circuitry 114 exercises control so that the potential of the filament 122b is equal to potential Pf32, which is higher than the intermediate potential Pg31. With this arrangement, the electrons generated from the filament 122a are emitted to the target 121, without being blocked by the intermediate potential Pg31. In contrast, the electrons generated from the filament 122b are blocked by the intermediate potential Pg31. In other words, the filament controlling circuitry 114 changes the filament(s) that emit electrons to the target 121 from "the filament 122a and the filament 122b" to "the filament 122a", by controlling the potential levels of the filaments, in conjunction with the switching of the tube voltage at the time T32.

As illustrated in FIG. 4, the filament controlling circuitry 114 is individually connected to each of the filaments 122a and 122b. Accordingly, the filament controlling circuitry 114 is able to control the potential levels of the filament 122a and the filament 122b with respect to the intermediate potential Pg31 for each filament and to thereby independently control the potential difference from the intermediate potential Pg31 for each filament.

Figure 7B:
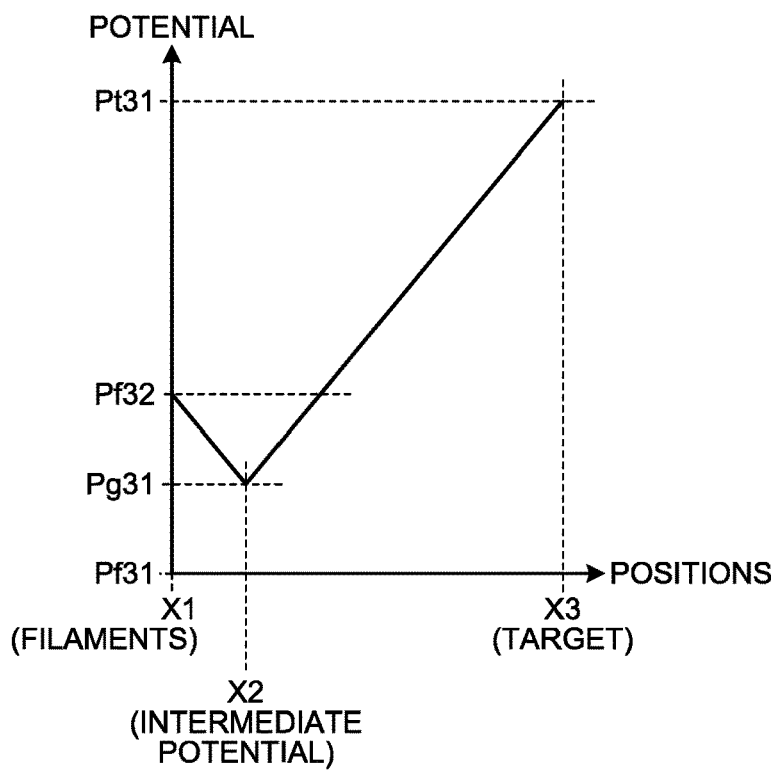
FIG. 7B is another chart for explaining the control over the filament potential according to the first embodiment.

Next, the potential Pf32 will be explained with reference to FIG. 7B. FIG. 7B is another chart for explaining the control over the filament potential according to the first embodiment. In FIG. 7B, the horizontal axis expresses positions, whereas the vertical axis expresses potential. As illustrated in FIG. 7B, the intermediate potential Pg31 is lower than the potential Pf32. In this situation, because the electrons generated from the filament 122b have a negative electric charge, the electrons move toward a position having higher potential. Accordingly, in the example in FIG. 7B, the electrons generated from the filament 122b in the position X1 do not move toward the position X2. In other words, by exercising control so that the potential of the filament 122b is equal to the potential Pf32, the filament controlling circuitry 114 is able to stop the emission of the electrons to the target 121 from the filament 122b having higher potential than the intermediate potential Pg31.

Returning to the description of FIG. 6, in the time period from the time T32 to the time T33, a tube current I32 flowing in the X-ray tube 12 has a value corresponding to the number of electrons generated from the filament 122a. In other words, as a result of the filament controlling circuitry 114 stopping the emission of the electrons from the filament 122b, the tube current I32 is decreased by an amount corresponding to the number of electrons generated from the filament 122b. Accordingly, the filament controlling circuitry 114 is able to maintain the radiation amount of the X-rays at the radiation amount D31 even after the tube voltage was switched at the time T32, by arranging the tube current I32 to have a smaller value than that of the tube current I31.

For example, the filament controlling circuitry 114 sets the tube current I31 and the tube current I32 smaller than the tube current I31 in advance, so that the radiation amount of the X-rays is constant before and after the switching of the tube voltage. Further, the filament controlling circuitry 114 maintains the radiation amount before and after the switching of the tube voltage, by changing the filament(s) that emit electrons to the target 121 in conjunction with the switching of the tube voltage and causing the tube current I31 and the tube current I32 that have been set to sequentially flow in the X-ray tube 12. The settings of the tube currents will be explained later.

Further, in the time period from the time T32 to the time T33, the X-ray detector 16 detects X-rays having passed through the patient P and having high energy. Further, at the time T33, the X-ray detector 16 reads an electric charge corresponding to the X-ray amount detected in the time period from the time T31 and the time T33 and outputs detection signals to the processing circuitry 20. In this situation, the reading process performed by the X-ray detector 16 at the time T33 is an example of the second reading process. Further, the image processing function 202 generates a high-energy image on the basis of the difference between the detection signals output at the time T33 and the detection signals output at the time T32. Further, the image processing function 202 performs a discriminating process on the substances contained in the patient P. For example, the image processing function 202 performs the discriminating process by calculating the difference between the low-energy image and the high-energy image or by inputting the low-energy image and the high-energy image to the trained model.

As illustrated in FIG. 6, the tube voltage controlling circuitry 112 switches the tube voltage while the X-ray tube 12 is radiating the X-ray pulse. With this arrangement, the tube voltage controlling circuitry 112 is able to acquire the low-energy image and the high-energy image in a short period of time and to thereby prevent the positional difference between the images.

Further, the filament controlling circuitry 114 changes the filament(s) that emit electrons to the target 121, by controlling the potential levels of the filament 122a and the filament 122b with respect to the intermediate potential Pg31 for each filament, in conjunction with the switching of the tube voltage. With this arrangement, the filament controlling circuitry 114 maintains the radiation amount of the X-rays before and after the switching of the tube voltage. In other words, the filament controlling circuitry 114 makes it possible to take the low-energy image and the high-energy image by using the same radiation amount. Consequently, the image processing function 202 is able to perform the discriminating process by using the low-energy image and the high-energy image. In other words, the image processing function 202 is able to perform the discriminating process on the basis of the results of the first reading process and the second reading process.

Next, settings of the tube voltage levels and the tube current values will be explained. For example, at first, the tube voltage controlling circuitry 112 sets the tube voltage V31 corresponding to the X-rays having low energy and the tube voltage V32 corresponding to the X-rays having high energy. In this situation, the tube voltage controlling circuitry 112 may set the tube voltage levels on the basis of input operations from the operator or may use values that are preset as the tube voltage levels.

Subsequently, the filament controlling circuitry 114 sets the tube current I31 caused to flow in the X-ray tube 12 while the tube voltage V31 is being supplied and the tube current I32 caused to flow in the X-ray tube 12 while the tube voltage V32 is being supplied. In other words, the filament controlling circuitry 114 sets the tube currents for time periods before and after the switching of the tube voltage. For example, the filament controlling circuitry 114 sets the tube current I31 and the tube current I32 so that the product of the tube voltage V31 and the tube current I31 is equal to the product of the tube voltage V32 and the tube current I32. In other words, the filament controlling circuitry 114 sets the tube current I31 and the tube current I32 that make the radiation amounts equal to each other, on the basis of the tube voltage V31 and the tube voltage V32.

In one example, the filament controlling circuitry 114, at first, obtains correspondence information R1 in which sets each made up of a tube voltage level and a tube current value are kept in correspondence with radiation amounts. The correspondence information R1 is, for example, generated in advance by the X-ray diagnostic apparatus 1 or another apparatus and stored in the memory 17. After that, the filament controlling circuitry 114 sets the tube current I31. In this situation, the filament controlling circuitry 114 may set the tube current I31 on the basis of an input operation from the operator or may use a value that is preset as a tube current for image taking processes of low-energy images.

After that, the filament controlling circuitry 114 obtains a radiation amount (the radiation amount D31) corresponding to the tube current I31 and the tube voltage V31 on the basis of the correspondence information R1. Subsequently, on the basis of the correspondence information R1, the filament controlling circuitry 114 obtains a tube current corresponding to the obtained radiation amount D31 and the tube voltage V32 and further sets the obtained tube current as the tube current I32. Although the example was explained in which the tube current I32 is set on the basis of the tube current I31, it is also acceptable to set the tube current I31 on the basis of the tube current I32.

Further, the filament controlling circuitry 114 sets a filament current (hereinafter, "filament current If31") of the filament 122a and a filament current (hereinafter, "filament current If32") of the filament 122b, on the basis of the tube voltage V31 and the tube voltage V32 as well as the tube current I31 and the tube current I32. In other words, the filament controlling circuitry 114 sets the temperatures of the filament 122a and the filament 122b.

For example, the filament controlling circuitry 114, at first, sets the filament current If31 on the basis of the tube current I32 and the tube voltage V32. More specifically, the filament controlling circuitry 114 sets the filament current If31 so that the current corresponding to the number of electrons generated from the filament 122a at the time of supplying the tube voltage V32 is equal to the tube current I32.

In one example, the filament controlling circuitry 114, at first, obtains correspondence information R2 in which sets each made up of a filament current value and a tube voltage level are kept in correspondence with tube current values. The correspondence information R2 is, for example, generated in advance by the X-ray diagnostic apparatus 1 or another apparatus and is stored in the memory 17. Further, the filament controlling circuitry 114 sets the filament current kept in correspondence with the tube voltage V32 and with the tube current I32 in the correspondence information R2, as the filament current If31.

Subsequently, the filament controlling circuitry 114 sets the filament current If32 on the basis of the filament current If31 that was set as well as the tube current I31 and the tube voltage V31. In this situation, the tube current I31 is equal to the sum of a current (hereinafter, "tube current I31a") corresponding to the number of electrons generated from the filament 122a at the time of supplying the tube voltage V31 and a current (hereinafter, "tube current I31b") corresponding to the number of electrons generated from the filament 122b at the time of supplying the tube voltage V31. Accordingly, the filament controlling circuitry 114 sets the filament current If32 so that the current corresponding to the number of electrons generated from the filament 122b at the time of supplying the tube voltage V31 is equal to the filament current I31b.

In one example, the filament controlling circuitry 114, at first, obtains the tube current kept in correspondence with the filament current If31 that was set and with the tube voltage V31 in the correspondence information R2, as the tube current I31a. Subsequently, the filament controlling circuitry 114 calculates the tube current I31b, by subtracting the tube current I31a from the tube current I31. Further, the controlling function 201 sets the filament current kept in correspondence with the tube voltage V31 and with the tube current I31b in the correspondence information R2, as the filament current If32.

As explained above, the tube voltage controlling circuitry 112 sets the tube voltage V31 and the tube voltage V32. Further, the filament controlling circuitry 114 sets the tube current I31 and the tube current I32, as well as the filament current If31 and the filament current If32. After these image taking conditions are set, the controlling function 201 performs the image taking processes to take the low-energy image and the high-energy image, by controlling the image taking system on the basis of the image taking conditions that have been set.

When an image taking process is to be performed, the filament controlling circuitry 114, at first, applies heat to the filaments by causing the filament current If31 to flow in the filament 122a and causing the filament current If32 to flow in the filament 122b. Further, the grid controlling circuitry 113 sets the intermediate potential Pg31 in a position between the filaments 122a and 122b and the target 121. Subsequently, the tube voltage controlling circuitry 112 sequentially supplies the tube voltage V31 and the tube voltage V32 to the X-ray tube 12.

In this situation, in conjunction with the switching from the tube voltage V31 to the tube voltage V32, the filament controlling circuitry 114 changes the filament(s) that emit electrons to the target 121 from "the filament 122a and the filament 122b" to "the filament 122a". With this arrangement, the filament controlling circuitry 114 is able to cause the tube currents set for the time periods before and after the switching of the tube voltage to flow in the X-ray tube 12. In other words, the filament controlling circuitry 114 is able to maintain the radiation amount of the X-rays before and after the switching of the tube voltage, by causing the tube current I31 to flow in the X-ray tube 12 while the tube voltage V31 is being supplied and causing the tube current I32 to flow in the X-ray tube 12 while the tube voltage V32 is being supplied.

Figure 8:
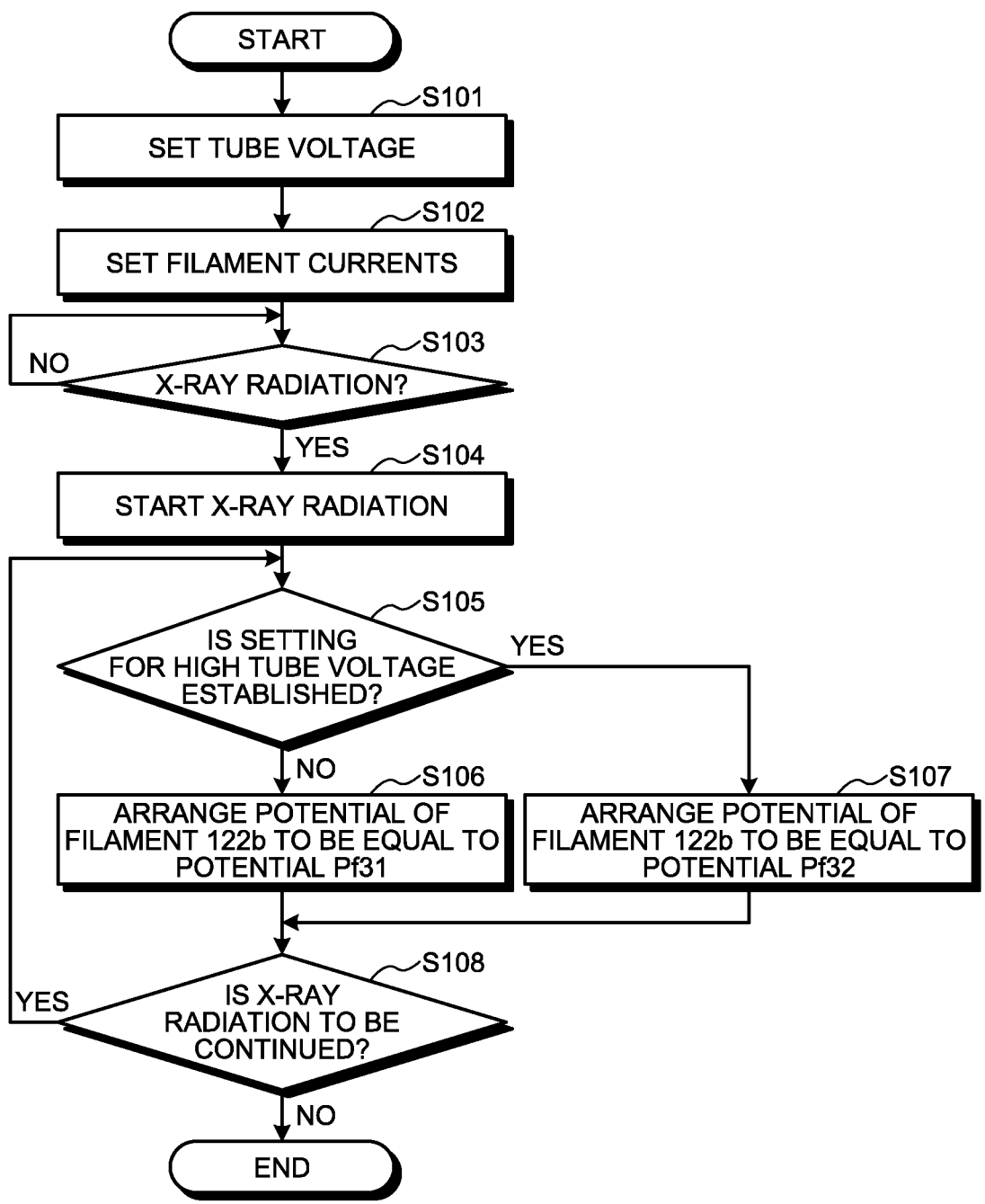
FIG. 8 is a flowchart for explaining a flow in a series of processes performed by the X-ray diagnostic apparatus according to the first embodiment.

Next, an example of a procedure in processes performed by the X-ray diagnostic apparatus 1 will be explained, with reference to FIG. 8. FIG. 8 is a flowchart for explaining a flow in the series of processes performed by the X-ray diagnostic apparatus 1 according to the first embodiment. Steps S101, S103, and S104 are steps corresponding to the tube voltage controlling circuitry 112. Steps S102, S105, S106, S107, and S108 are steps corresponding to the filament controlling circuitry 114.

At first, the tube voltage controlling circuitry 112 sets tube voltage (step S101). For example, the tube voltage controlling circuitry 112 sets the tube voltage V31 corresponding to the X-rays having low energy and the tube voltage V32 corresponding to the X-rays having high energy. Subsequently, the filament controlling circuitry 114 sets tube currents for the time periods before and after the switching of the tube voltage, on the basis of the tube voltage levels that were set and further sets a filament current for each of the filaments 122a and 122b (step S102).

After that, the tube voltage controlling circuitry 112 judges whether or not X-ray radiation is to be performed (step S103). When no X-ray radiation is to be performed (step S103: No), the tube voltage controlling circuitry 112 transitions into a standby state. On the contrary, when X-ray radiation is to be performed (step S103: Yes), the tube voltage controlling circuitry 112 supplies tube voltage to the X-ray tube 12 and starts the X-ray radiation (step S104). For example, when an X-ray radiation button included in the input interface 19 is pressed by the operator, the tube voltage controlling circuitry 112 determines that X-ray radiation is to be performed and starts radiating X-rays.

In this situation, the filament controlling circuitry 114 judges whether or not the setting for high tube voltage is established (step S105). When the setting is established not for high tube voltage, but for low tube voltage (step S105: No), the filament controlling circuitry 114 arranges the potential levels of the filament 122a and the filament 122b to be equal to the potential Pf31, which is lower than the intermediate potential Pg31 (step S106). In other words, the filament controlling circuitry 114 causes electrons to be emitted from the filament 122a and the filament 122b to the target 121.

On the contrary, when the setting is established for high tube voltage (step S105: Yes), the filament controlling circuitry 114 arranges the potential of the filament 122a to be equal to the potential Pf31 and also arranges the potential of the filament 122b to be equal to the potential Pf32, which is higher than the intermediate potential Pg31 (step S107). In other words, the filament controlling circuitry 114 causes electrons to be emitted, to the target 121, from the filament 122a having lower potential than the intermediate potential Pg31, and stops the emission of the electrons to the target 121 from the filament 122b having higher potential than the intermediate potential Pg31.

After step S106 or step S107, the tube voltage controlling circuitry 112 judges whether or not the X-ray radiation is to be continued (step S108). When the X-ray radiation is to be continued (step S108: Yes), the filament controlling circuitry 114 returns to step S105 and judges whether or not the setting is established for high tube voltage. On the contrary, when the X-ray radiation is not to be continued (step S108: No), the tube voltage controlling circuitry 112 and the filament controlling circuitry 114 end the process.

As explained above, according to the first embodiment, the X-ray tube 12 includes: the target 121 configured to generate the X-rays in response to the emission of electrons thereto; the filament 122a and the filament 122b configured to emit the electrons into substantially the same position on the target 121; and one selected from between the grid 123a and the grid 123b configured to be used in common by the filament 122a and the filament 122b. Further, the tube voltage controlling circuitry 112 is configured to control the tube voltage to be supplied to the X-ray tube 12. Further, the grid controlling circuitry 113 is configured to set the intermediate potential Pg in the position between the filaments 122a and 122b and the target 121, by controlling the one selected from between the grid 123a and the grid 123b. Further, in conjunction with the switching of the tube voltage, the filament controlling circuitry 114 is configured to change the filament(s) that emit electrons to the target 121 between the filament 122a and the filament 122b, by controlling the potential levels of the filament 122a and the filament 122b with respect to the intermediate potential Pg for each filament. Accordingly, the X-ray diagnostic apparatus 1 according to the first embodiment is able to appropriately control the tube currents at the time of the switching of the tube voltage.

In other words, when the tube voltage is switched without changing the filament(s) that emit electrons to the target 121, the tube current would also increase or decrease in conjunction with the increase or the decrease of the tube voltage. For example, when the tube voltage is switched from low tube voltage to high tube voltage, the tube current would also increase as the tube voltage increases. As a result, because the radiation amounts of the X-rays used in the image taking processes would significantly be different between the low-energy image and the high-energy image, it might be impossible to perform the discriminating process in some situations. In contrast, the X-ray diagnostic apparatus 1 according to the first embodiment is configured to appropriately control the tube currents by changing the filament(s) that emit electrons to the target 121 in conjunction with the switching of the tube voltage and is therefore able to keep constant the radiation amount of the X-rays used for the image taking processes between the low-energy image and the high-energy image. Accordingly, the X-ray diagnostic apparatus 1 makes it possible to perform the discriminating process by using the low-energy image and the high-energy image.

Further, the X-ray diagnostic apparatus 1 according to the first embodiment is configured to control the tube currents by controlling the potential levels of the filament 122a and the filament 122b, for each filament. Consequently, the X-ray diagnostic apparatus is able to change the tube current in a shorter period of time compared to the situation where the tube current is controlled by heating or cooling the filaments. For example, even in the situation where the tube voltage is switched while the X-ray tube 12 is radiating an X-ray pulse, the X-ray diagnostic apparatus 1 is able to appropriately control the tube currents. With these arrangements, the X-ray diagnostic apparatus 1 is able to prevent the positional difference between the low-energy image and the high-energy image. Consequently, the X-ray diagnostic apparatus 1 makes it possible to perform the discriminating process on a site having much movement.

Further, as explained above, the X-ray tube 12 includes the plurality of filaments configured to emit the electrons into substantially the same position on the target 121. In other words, the plurality of filaments included in the X-ray tube 12 have substantially the same focal point. Accordingly, even when the filament(s) that emit electrons to the target 121 are changed, the X-ray tube 12 is able to radiate the X-rays, without changing the position or the angle with respect to the patient P. For example, even when the filament(s) that emit electrons to the target 121 are changed between the time of the low-energy image taking process and the time of the high-energy image taking process, the X-ray tube 12 is able to yield the low-energy image and the high-energy as images of mutually the same angle and mutually the same position. With these arrangements, the X-ray diagnostic apparatus 1 makes it possible to perform the discriminating process by using the low-energy image and the high-energy image.

Further, as explained above, the filament controlling circuitry 114 is configured to change the filament(s) that emit electrons to the target 121 between the plurality of filaments, by controlling the potential levels of the plurality of filaments with respect to the intermediate potential Pg for each filament. In other words, the X-ray diagnostic apparatus 1 according to the first embodiment is able to appropriately control the tube currents by setting the single intermediate potential Pg. For example, by using a single grid, the X-ray diagnostic apparatus 1 is able to appropriately control the tube currents.

Further, as explained above, the filament controlling circuitry 114 is configured to set the tube currents for the time periods before and after the switching of the tube voltage to be supplied to the X-ray tube 12, on the basis of the correspondence information R1 in which the sets each made up of a tube voltage level and a tube current value are kept in correspondence with radiation amounts. Further, the filament controlling circuitry 114 is configured to maintain the radiation amount of the X-rays before and after the switching of the tube voltage by changing the filament(s) that emit electrons to the target 121 in conjunction with the switching of the tube voltage and further causing the tube currents set for the time periods before and after the switching of the tube voltage to flow in the X-ray tube 12. Accordingly, the filament controlling circuitry 114 is able to set the tube currents with respect to the arbitrary tube voltage levels and is able to exercise control to maintain the radiation amount before and after the switching of the tube voltage.

Figure 9:
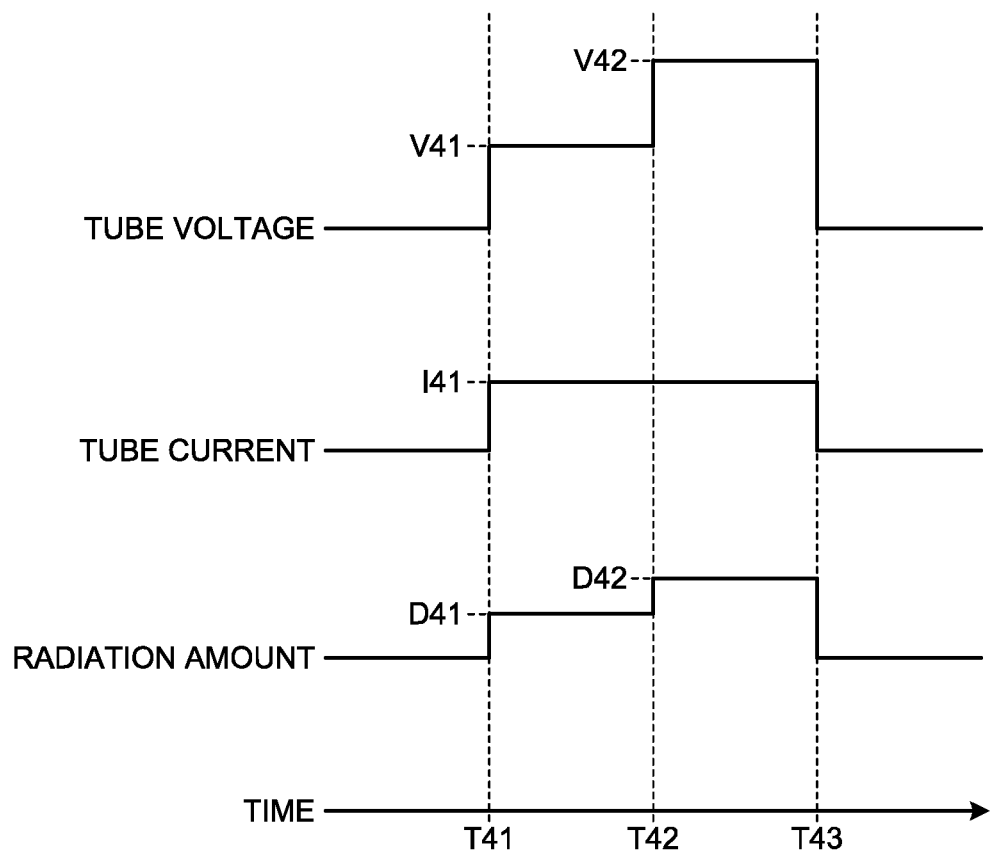
FIG. 9 is a chart illustrating yet another example of the dual-energy acquisition according to the first embodiment.

Further, in the embodiments described above, the example is explained in which the radiation amount of the X-rays is maintained before and after the switching of the tube voltage; however, possible embodiments are not limited to this example. For instance, the filament controlling circuitry 114 may be configured to maintain the tube current in the X-ray tube 12 before and after the switching of the tube voltage. This example will be explained below, with reference to FIG. 9. FIG. 9 is a chart illustrating yet another example of the dual-energy acquisition according to the first embodiment. FIG. 9 illustrates the example in which the tube voltage to be supplied to the X-ray tube 12 is switched between tube voltage V41 and tube voltage V42. The tube voltage V41 corresponds to X-rays having low energy. In contrast, the tube voltage V42 is voltage higher than the tube voltage V41 and corresponds to X-rays having high energy.

In one example, the tube voltage controlling circuitry 112, at first, sets the tube voltage V41 to be supplied to the X-ray tube 12 in the time period from the time T41 to the time T42 and the tube voltage V42 to be supplied to the X-ray tube 12 in the time period from the time T42 to the time T43. Subsequently, on the basis of the tube voltage V41 and the tube voltage V42, the filament controlling circuitry 114 sets a filament current If41 of the filament 122a and a filament current If42 of the filament 122b, so that the tube current is constant over the time period from the time T41 to the time T42 and the time period from the time T42 to the time T43.

For example, the filament controlling circuitry 114 sets the filament current If41 so that the current corresponding to the number of electrons generated from the filament 122a at the time of supplying the tube voltage V42 is equal to the tube current I41. For example, the filament controlling circuitry 114 sets the filament current kept in correspondence with the tube voltage V42 and with the tube current I41 in the correspondence information R2 in which the sets each made up of a filament current value and a tube voltage level are kept in correspondence with tube currents, as the filament current If41.

Subsequently, the filament controlling circuitry 114 sets the filament current If42 so that the sum of the current (a tube current I41a) corresponding to the number of electrons generated from the filament 122a at the time of supplying the tube voltage V41 and the current (a tube current I41b) corresponding to the number of electrons generated from the filament 122b at the time of supplying the tube voltage V41 is equal to the tube current I41. For example, the filament controlling circuitry 114 obtains the tube current kept in correspondence with the filament current If41 that was set and with the tube voltage V41 in the correspondence information R2, as the tube current I41a. After that, the filament controlling circuitry 114 calculates the tube current I41b, by subtracting the tube current I41a from the tube current I41. After that, the filament controlling circuitry 114 sets the filament current kept in correspondence with the tube voltage V41 and with the tube current I41b in the correspondence information R2, as the filament current If42.

When an image taking process is to be performed, the filament controlling circuitry 114, at first, applies heat to the filaments by causing the filament current If41 to flow in the filament 122a and causing the filament current If42 to flow in the filament 122b. Further, the grid controlling circuitry 113 sets intermediate potential Pg41 in a position between the filaments 122a and 122b and the target 121. Subsequently, the tube voltage controlling circuitry 112 sequentially supplies the tube voltage V41 and the tube voltage V42 to the X-ray tube 12.

In this situation, in conjunction with the switching from the tube voltage V41 to the tube voltage V42, the filament controlling circuitry 114 changes the filament(s) that emit electrons to the target 121 from "the filament 122a and the filament 122b" to "the filament 122a". With this arrangement, the filament controlling circuitry 114 is able to maintain the tube current in the X-ray tube 12 at the tube current I41 before and after the switching of the tube voltage.

Further, in the time period from the time T41 to the time T42, the X-ray detector 16 detects X-rays having passed through the patient P and having low energy. Further, at the time T42, the X-ray detector 16 reads an electric charge corresponding to the X-ray amount detected in the time period from the time T41 to the time T42 and outputs detection signals to the processing circuitry 20. In this situation, the X-ray detector 16 performs a non-destructive reading process. Further, the image processing function 202 generates a low-energy image, on the basis of the detection signals output from the X-ray detector 16.

Further, in the time period from the time T42 to the time T43, the X-ray detector 16 detects X-rays having passed through the patient P and having high energy. Further, at the time T43, the X-ray detector 16 reads an electric charge corresponding to the X-ray amount detected in the time period from the time T41 to the time T43 and outputs detection signals to the processing circuitry 20. Further, the image processing function 202 calculates the difference between the detection signals output at the time T43 and the detection signals output at the time T42. After that, on the basis of the signals of the calculated difference, the image processing function 202 generates a high-energy image.

In the example in FIG. 9, although the tube current is maintained before and after the switching of the tube voltage, the radiation amount of the X-rays changed. More specifically, as a result of the tube voltage being switched from the tube voltage V41 to the tube voltage V42 at the time T42, the radiation amount of the X-rays increased from a radiation amount D41 to a radiation amount D42.

Accordingly, the filament controlling circuitry 114 is able to control the tube currents in accordance with purposes of the low-energy image and the high-energy image. For example, the filament controlling circuitry 114 is able to make equal the counts of X-ray photons at the time of the image taking processes between the low-energy image and the high-energy image, by maintaining the tube current before and after the switching of the tube voltage. As a result, the filament controlling circuitry 114 is able to make the Signal-to-Noise Ratio (SNR) approximately equal between the low-energy image and the high-energy image. Accordingly, when stabilizing the signal-to-noise ratios of the images is prioritized, the filament controlling circuitry 114 exercises control so as to maintain the tube current before and after the switching of the tube voltage as illustrated in FIG. 9. In contrast, when stabilizing the radiation amounts of the images is prioritized, for example, when a discriminating process is performed by calculating the difference between the low-energy image and the high-energy image, the filament controlling circuitry 114 exercises control so as to maintain the radiation amount before and after the switching of the tube voltage as illustrated in FIG. 6.

Besides the control to maintain the radiation amount before and after the switching of the tube voltage and the control to maintain the tube voltage before and after the switching of the tube voltage, the filament controlling circuitry 114 is capable of exercising other various types of control. For example, in accordance with what is prioritized, the filament controlling circuitry 114 is able to exercise such control that is in-between the control to maintain the radiation amount before and after the switching of the tube voltage and the control to maintain the tube voltage before and after the switching of the tube voltage.

In one example, when it is desirable to stabilize both the radiation amounts and the signal-to-noise ratios of the images, the filament controlling circuitry 114 exercises the control that is in-between the control to maintain the radiation amount before and after the switching of the tube voltage and the control to maintain the tube voltage before and after the switching of the tube voltage. For example, at the time T42 illustrated in FIG. 9, the filament controlling circuitry 114 decreases the tube current in the X-ray tube 12 from the tube current I41 to a tube current I41'. In other words, the filament controlling circuitry 114 arranges the tube current in the time period from the time T42 to the time T43 to be equal to the tube current I41', which is smaller than the tube current I41. As a result, the radiation amount in the time period from the time T42 to the time T43 has a value closer to the radiation amount D41 than to the radiation amount D42. In this situation, the filament controlling circuitry 114 is able to adjust the tube current I41' in accordance with what is prioritized. For example, the filament controlling circuitry 114 exercises control so that the higher the level of priority of the signal-to-noise ratios is, the larger will be the value of the tube current I41'; and so that the higher the level of priority of the radiation amounts is, the smaller will be the value of the tube current I41'.

Further, in the embodiments described above, the example is explained in which the filament(s) that emit electrons to the target 121 are changed in conjunction with the switching from the low tube voltage to the high tube voltage; however, possible embodiments are not limited to this example. The filament controlling circuitry 114 may change the filament(s) that emit electrons to the target 121, in conjunction with switching from high tube voltage to low tube voltage.

Further, in the embodiments described above, the example is explained in which the filament(s) that emit electrons to the target 121 are changed from "the filament 122a and the filament 122b" to "the filament 122a" in conjunction with the switching of the tube voltage; however, possible embodiments are not limited to this example. The filament controlling circuitry 114 is able to make various changes to the combination of filaments to emit electrons to the target 121.

For example, in conjunction with the switching of the tube voltage, the filament controlling circuitry 114 may change the filament(s) that emit electrons to the target 121 from "the filament 122a and the filament 122b" to "the filament 122b", may change from "the filament 122a" to "the filament 122a and the filament 122b", or may change from "the filament 122b" to "the filament 122a and the filament 122b".

Further, the filament controlling circuitry 114 does not necessarily have to change the combination of filaments to emit electrons to the target 121 and may be configured to switch the filament that emits electrons to the target 121. In other words, in conjunction with the switching of the tube voltage, the filament controlling circuitry 114 may switch the filament that emits electrons to the target 121 from "the filament 122a" to "the filament 122b" or from "the filament 122b" to "the filament 122a".

Further, in the embodiments described above, the example is explained in which the tube voltage is switched once while the X-ray tube 12 is radiating the X-ray pulse; however, possible embodiments are not limited to this example. The tube voltage controlling circuitry 112 may switch the tube voltage multiple times while the X-ray tube 12 is radiating an X-ray pulse. In that situation, the filament controlling circuitry 114 is able to change the filament(s) that emit electrons to the target 121, each of the multiple times when the tube voltage is switched.

As an example, a situation will be explained in which the tube voltage is switched among tube voltage V51, tube voltage V52 higher than the tube voltage V51, and tube voltage V53 higher than the tube voltage V52. In other words, in the present example, a Multi-Energy (ME) acquisition is performed by using the three types of X-rays. For example, the filament controlling circuitry 114, at first, applies heat to the filament 122a by using a filament current If51, and also applies heat to the filament 122b by using a filament current If52, which is larger than the filament current If51. In other words, the filament controlling circuitry 114 exercises control so that the filament 122b has higher temperature than the filament 122a.

Subsequently, the tube voltage controlling circuitry 112 supplies the tube voltage V51 to the X-ray tube 12. In this situation, the filament controlling circuitry 114 causes electrons to be emitted to the target 121 from "the filament 122a and the filament 122b", by exercising control so that the potential levels of the filament 122a and the filament 122b are lower than the intermediate potential Pg. As a result, the filament controlling circuitry 114 arranges the tube current in the X-ray tube 12 to be equal to a tube current I51.

After that, the tube voltage controlling circuitry 112 switches the tube voltage to be supplied to the X-ray tube 12 from the tube voltage V51 to the tube voltage V52. Further, in conjunction with the switching of the tube voltage, the filament controlling circuitry 114 changes the filament(s) that emit electrons to the target 121 from "the filament 122a and the filament 122b" to "the filament 122b". As a result, the filament controlling circuitry 114 maintains the radiation amount of the X-rays before and after the switching of the tube voltage by decreasing the tube current in the X-ray tube 12 from the tube current I51 to a tube current I52.

After that, the tube voltage controlling circuitry 112 switches the tube voltage to be supplied to the X-ray tube 12 from the tube voltage V52 to the tube voltage V53. Further, in conjunction with the switching of the tube voltage, the filament controlling circuitry 114 switches the filament that emits electrons to the target 121, from "the filament 122b" to "the filament 122a". As a result, the filament controlling circuitry 114 maintains the radiation amount of the X-rays before and after the switching of the tube voltage, by decreasing the tube current in the X-ray tube 12 from the tube current I52 to a tube current I53.

Although the example is explained above in which the tube voltage is sequentially increased while the X-ray pulse is being radiated, the tube voltage controlling circuitry 112 may be configured to sequentially decrease the tube voltage. In other words, the tube voltage controlling circuitry 112 may switch the tube voltage to be supplied to the X-ray tube 12 from the tube voltage V53 to the tube voltage V52, and then from the tube voltage V52 to the tube voltage V51. In that situation, in conjunction with the switching of the tube voltage, the filament controlling circuitry 114 switches the filament(s) that emit electrons to the target 121 from "the filament 122a" to "the filament 122b" and further from "the filament 122b" to "the filament 122a and the filament 122b".

In another example, the tube voltage controlling circuitry 112 may be configured to switch the tube voltage so that the waveform of the X-ray pulse has a convex shape or a concave shape. For example, to arrange the waveform of the X-ray pulse to have a convex shape, the tube voltage controlling circuitry 112 switches the tube voltage to be supplied to the X-ray tube 12, from the tube voltage V51 to the tube voltage V53, and then from the tube voltage V53 to the tube voltage V52. In that situation, in conjunction with the switching of the tube voltage, the filament controlling circuitry 114 switches the filament(s) that emit electrons to the target 121 from "the filament 122a and the filament 122b" to "the filament 122a" and further from "the filament 122a" to "the filament 122b".

Figure 10A:
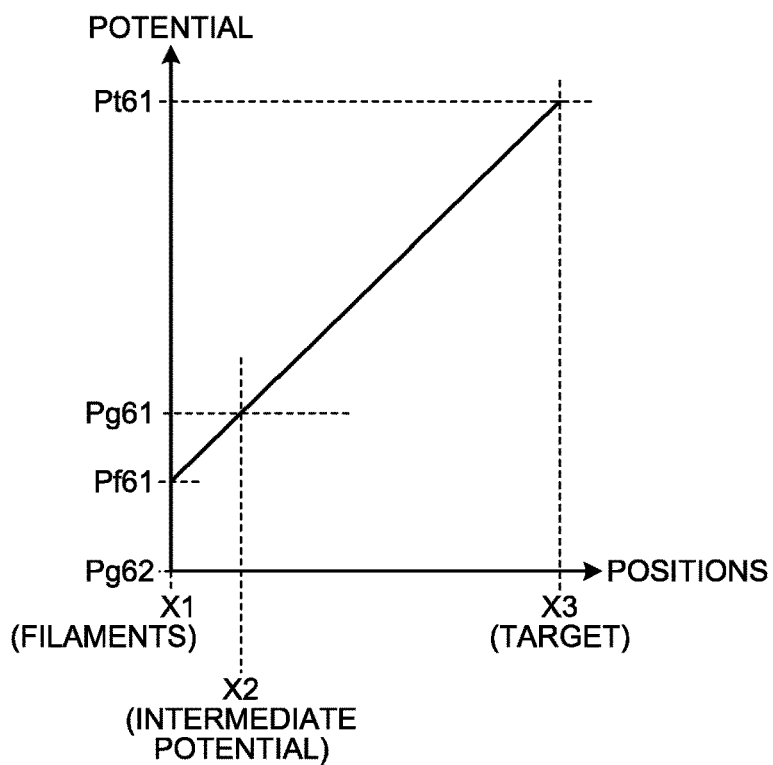
FIG. 10A is a chart for explaining control over intermediate potential according to the first embodiment.
Figure 10B:
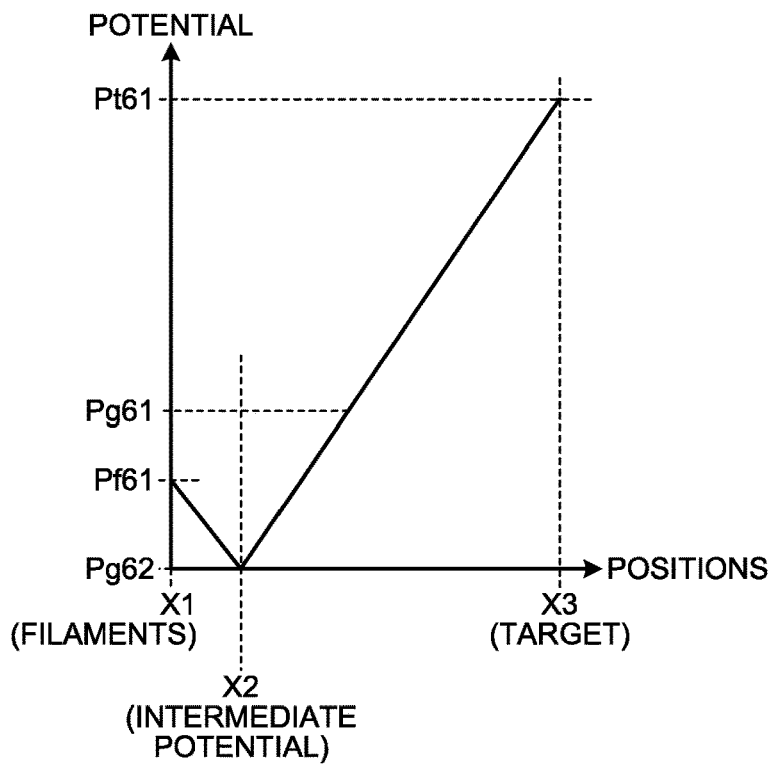
FIG. 10B is another chart for explaining the control over the intermediate potential according to the first embodiment.

Further, in the embodiments above, the example is explained in which the filament(s) that emit electrons to the target 121 are changed between the filament 122a and the filament 122b, by controlling the potential levels of the filament 122a and the filament 122b with respect to the intermediate potential Pg for each filament. In contrast, it may also be an idea to set intermediate potential Pg for each of the filaments and to change the filament(s) that emit electrons to the target 121 between the filament 122a and the filament 122b, by controlling the intermediate potentials Pg with respect to the potential of each of the filaments 122a and 122b. This example will be explained with reference to FIGS. 10A and 10B. FIGS. 10A and 10B are charts for explaining the control over the intermediate potential according to the first embodiment.

As indicated on the horizontal axis in FIGS. 10A and 10B, the filament 122a and the filament 122b are in the position X1. In FIGS. 10A and 10B, the potential of each of the filaments 122a and 122b is expressed as potential Pf61. Further, the target 121 is in the position X3. In FIGS. 10A and 10B, the potential of the target 121 is expressed as potential Pt61.

Further, in FIGS. 10A and 10B, intermediate potential Pg is set for each of the filaments 122a and 122b. For example, the X-ray tube 12 includes as many grids as the number of filaments. In the following sections, an example will be explained in which the X-ray tube 12 includes: a grid 123c corresponding to the filament 122a; and another grid 123d corresponding to the filament 122b. The grid controlling circuitry 113 sets intermediate potential Pg for each of the filaments 122a and 122b, by controlling each of the grids 123c and 123d.

For example, the grid controlling circuitry 113 sets intermediate potential Pg61 illustrated in FIG. 10A by controlling the grid 123c. In other words, by controlling the grid 123c, the grid controlling circuitry 113 sets the intermediate potential Pg61, which is higher than the potential Pf61 of the filament 122a, in a position between the filament 122a and the target 121. As a result, the electrons generated from the filament 122a in the position X1 pass through the position X2 and are emitted to the target 121 in the position X3.

Further, for example, by controlling the grid 123d, the grid controlling circuitry 113 sets intermediate potential Pg62 illustrated in FIG. 10B. In other words, by controlling the grid 123d, the grid controlling circuitry 113 sets intermediate potential Pg62, which is lower than the potential Pf61 of the filament 122b, in a position between the filament 122b and the target 121. As a result, the electrons generated from the filament 122b in the position X1 are blocked by the intermediate potential Pg62.

In this situation, by controlling the grid 123c and changing the intermediate potential Pg in the position between the filament 122a and the target 121 from the intermediate potential Pg61 to the intermediate potential Pg62, the grid controlling circuitry 113 is able to stop the emission of the electrons from the filament 122a to the target 121. Further, by controlling the grid 123d and changing the intermediate potential Pg in the position between the filament 122b and the target 121 from the intermediate potential Pg62 to the intermediate potential Pg61, the grid controlling circuitry 113 is able to cause electrons to be emitted from the filament 122b to the target 121. In other words, by using the grid 123c and the grid 123d and setting the plurality of mutually-different intermediate potential levels Pg in the positions that are between each of the filament 122a and 122b and the target 121, the grid controlling circuitry 113 changes the filament(s) that emit electrons to the target 121 between the filament 122a and the filament 122b. For example, in conjunction with the switching of the tube voltage, the grid controlling circuitry 113 changes the quantity of filaments that emit electrons to the target 121, by controlling the same or mutually-different levels of intermediate potential Pg.

As explained with reference to FIGS. 10A and 10B, the grid controlling circuitry 113 is able to control whether or not electrons are emitted from each of the filaments to the target 121, by controlling the intermediate potential Pg set for each of the filaments. In other words, the grid controlling circuitry 113 is able to change the filament(s) that emit electrons to the target 121 between the filament 122a and the filament 122b, by controlling the intermediate potential Pg set for each of the filaments.

The examples have so far been explained in which the filament controlling circuitry 114 changes the filament(s) that emit electrons to the target 121 by controlling the potential levels of the filament 122a and the filament 122b or the grid controlling circuitry 113 changes the filament(s) that emit electrons to the target 121 by controlling the intermediate potential Pg. However, possible embodiments are not limited to this example. For instance, another arrangement is also acceptable in which the filament(s) that emit electrons to the target 121 are changed as a result of the filament controlling circuitry 114 controlling the potential levels of the filament 122a and the filament 122b and also the grid controlling circuitry 113 controlling the intermediate potential Pg. In the following sections, the filament controlling circuitry 114 and the grid controlling circuitry 113 may collectively be referred to as changing circuitry. In other words, the changing circuitry is configured to change the filament(s) that emit electrons to the target 121 between the filament 122a and the filament 122b by controlling one or both of the same or mutually-different levels of intermediate potential Pg and the potential levels of the plurality of filaments.

In the first embodiment described above, the example is explained in which the X-ray tube 12 includes the two filaments (the filament 122a and the filament 122b). In contrast, in a second embodiment, an example will be explained in which the X-ray tube 12 includes three or more filaments. Some of the constituent elements that have the same configurations as those explained in the first embodiment will be referred to by using the same reference characters as those in FIG. 1 or 4, and the explanations thereof will be omitted.

As an example, a situation will be explained below in which the X-ray tube 12 further includes a filament 122c, in addition to the filament 122a and the filament 122b illustrated in FIG. 4. In other words, the following will describe the example in which the X-ray tube 12 includes the three filaments. Further, in the present embodiment, the example will be explained in which the X-ray tube 12 includes the grid 123a or the grid 123b. In other words, in the present embodiment, the X-ray tube 12 includes a grid used in common among the filament 122a, the filament 122b, and the filament 122c. Further, in the present embodiment, the example will be explained in which the filament controlling circuitry 114 changes the filament(s) that emit electrons to the target 121 by controlling the potential levels of the plurality of filaments for each filament.

Figure 11:
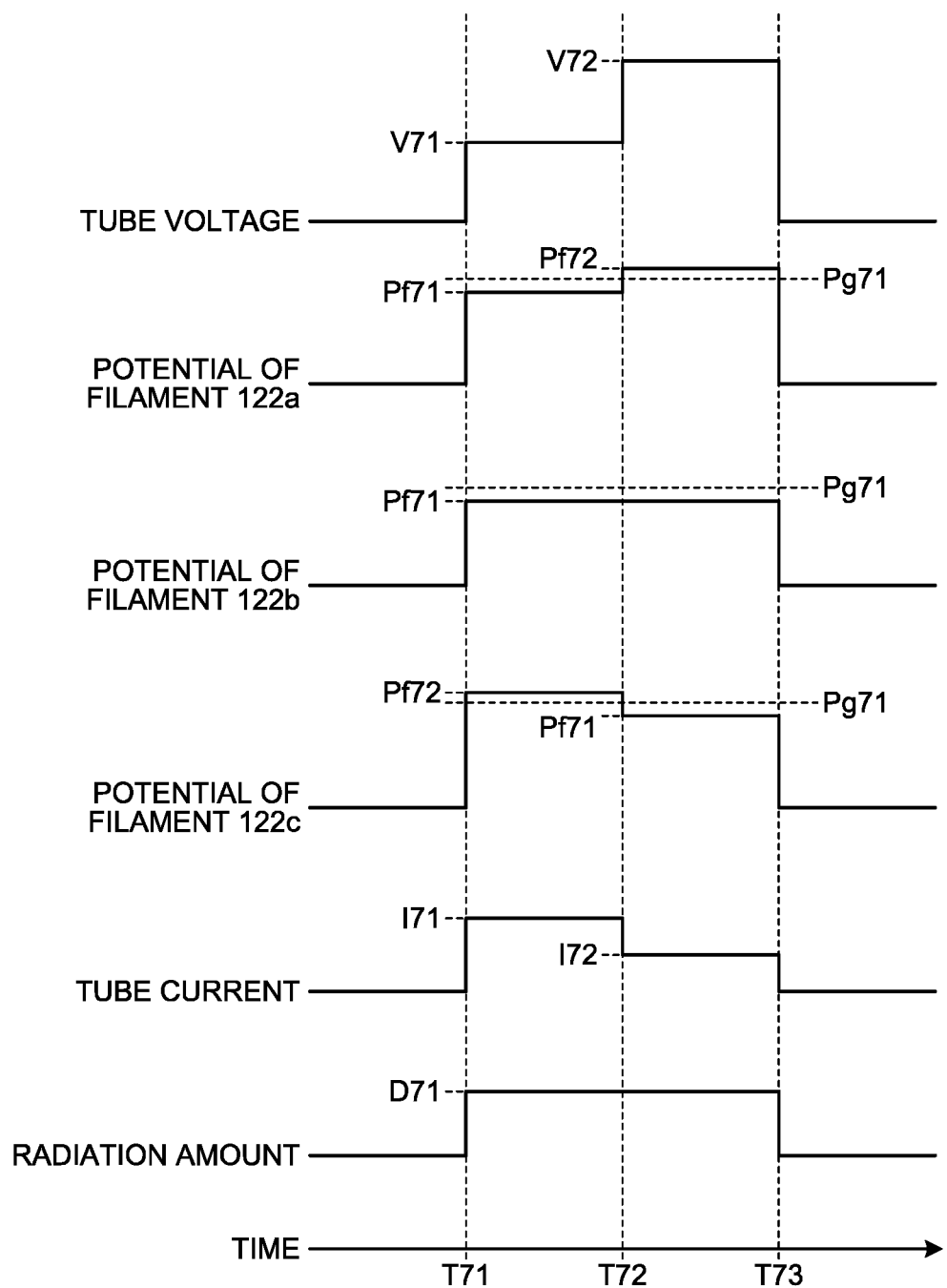
FIG. 11 is a chart illustrating an example of a dual-energy acquisition according to a second embodiment.

The tube voltage controlling circuitry 112, at first, sets tube voltage V71 and tube voltage V72 illustrated in FIG. 11. Subsequently, the filament controlling circuitry 114 sets a tube current I71 and a tube current I72 on the basis of the tube voltage V71 and the tube voltage V72. For example, on the basis of the correspondence information R1 in which the sets each made up of a tube voltage level and a tube current value are kept in correspondence with radiation amounts, the filament controlling circuitry 114 sets the tube current I71 and the tube current I72 so that the radiation amount is constant before and after the switching of the tube voltage. FIG. 11 is a chart illustrating an example of a dual-energy acquisition according to the second embodiment.

Subsequently, on the basis of the tube voltage V71 and the tube voltage V72 as well as the tube current I71 and the tube current I72, the filament controlling circuitry 114 sets a filament current (hereinafter, "filament current If71") of the filament 122a, a filament current (hereinafter, "filament current If72") of the filament 122b, and a filament current (hereinafter "filament current If73") of the filament 122c. The filament controlling circuitry 114 is individually connected to each of the filaments 122a, 122b, and 122c. With these arrangements, the filament controlling circuitry 114 is able to cause mutually-different filament currents to flow in the filament 122a, the filament 122b, and the filament 122c.

In the example in FIG. 11, the filament controlling circuitry 114 sets the filament current If71, the filament current If72, and the filament current If73, so that the sum of the current (hereinafter, "tube current I71a") corresponding to the number of electrons generated from the filament 122a at the time of supplying the tube voltage V71 and the current (hereinafter, "tube current I71b") corresponding to the number of electrons generated from the filament 122b at the time of supplying the tube voltage V71 is equal to the tube current I71, whereas the sum of the current (hereinafter, "tube current I72b") corresponding to the number of electrons generated from the filament 122b at the time of supplying the tube voltage V72 and the current (hereinafter, "tube current I72c") corresponding to the number of electrons generated from the filament 122c at the time of supplying the tube voltage V71 is equal to the tube current I72.

The tube current I71a has a value corresponding to the filament current If71 and the tube voltage V71 (Relational Expression 1). The tube current I71b has a value corresponding to the filament If72 and the tube voltage V71 (Relational Expression 2). The tube current I72b has a value corresponding to the filament current If72 and the tube voltage V72 (Relational Expression 3). The tube current I72c has a value corresponding to the filament current If73 and the tube voltage V72 (Relational Expression 4). Further, the tube current I71 is equal to the sum of the tube current I71a and the tube current I71b (Relational Expression 5). The tube current I72 is equal to the sum of the tube current I72b and the tube current I72c (Relational Expression 6). In the example in FIG. 11, there are seven unknown numbers (the filament current If71, the filament current If72, the filament current If73, the tube current I71a, the tube current I71b, the tube current I72b, and the tube current I72c) for these six relational expressions. In other words, the filament controlling circuitry 114 is unable to set the filament current If71, the filament current If72, and the filament current If73 by using only the six relational expressions presented above.

Accordingly, the filament controlling circuitry 114 sets the filament current If71, the filament current If72, and the filament current If73, by using additional conditions with the six relational expressions. For example, the filament controlling circuitry 114 sets the filament current If71, the filament current If72, and the filament current If73 so that while the six relational expressions are satisfied, the sum of the filament current If71, the filament current If72, and the filament current If73 is at a minimum. With this arrangement, the filament controlling circuitry 114 is able to prevent the filaments from being deteriorated by the applied heat.

Further, for example, the filament controlling circuitry 114 sets the filament current If71, the filament current If72, and the filament current If73 so that while the six relational expressions are satisfied, the variance value of the filament current If71, the filament current If72, and the filament current If73 is at a minimum. With this arrangement, the filament controlling circuitry 114 is able to arrange the degrees of deterioration of the filaments caused by the applied heat to be approximately equal among the filaments.

When an image taking process is to be performed, the filament controlling circuitry 114, at first, applies heat to the filaments, by causing the filament current If71 to flow in the filament 122a, causing the filament current If72 to flow in the filament 122b, and causing the filament current If73 to flow in the filament 122c. Further, the grid controlling circuitry 113 sets intermediate potential Pg71 in a position between the filaments 122a, 122b, and 122c and the target 121.

Subsequently, in the time period from the time T71 to the time T72, the tube voltage controlling circuitry 112 supplies the tube voltage V71 to the X-ray tube 12. In this situation, the filament controlling circuitry 114 exercises control so that the potential of the filament 122a and the potential of the filament 122b are each equal to potential Pf71, which is lower than the intermediate potential Pg71. As a result, the electrons generated from the filament 122a and the filament 122b are emitted to the target 121 without being blocked by the intermediate potential Pg71. Further, the filament controlling circuitry 114 exercises control so that the potential of the filament 122c is equal to potential Pf72, which is higher than the intermediate potential Pg71. As a result, electrons generated from the filament 122c are blocked by the intermediate potential Pg71.

In other words, in the time period from the time T71 to the time T72, the filament controlling circuitry 114 causes the electrons to be emitted from the filament 122a and the filament 122b to the target 121 and stops the emission of the electrons from the filament 122c to the target 121. As a result, in the time period from the time T71 to the time T72, the filament controlling circuitry 114 arranges the tube current in the X-ray tube 12 to be equal to the tube current I71.

Further, the filament controlling circuitry 114 is individually connected to each of the filaments 122a, 122b, and 122c. Accordingly, the filament controlling circuitry 114 is able to control the potential levels of the filament 122a, the filament 122b, and the filament 122c with respect to the intermediate potential Pg71 for each filament and to thereby independently control the potential difference from the intermediate potential Pg71 for each filament.

Further, in the time period from the time T71 to the time T72, the X-ray detector 16 detects X-rays having passed through the patient P and having low energy. Further, at the time T72, the X-ray detector 16 reads an electric charge corresponding to the X-ray amount detected in the time period from the time T71 to the time T72 and outputs detection signals to the processing circuitry 20. In this situation, the X-ray detector 16 performs a non-destructive reading process. Further, the image processing function 202 generates a low-energy image on the basis of the detection signals output from the X-ray detector 16.

Further, at the time T72, the tube voltage controlling circuitry 112 switches the tube voltage to be supplied to the X-ray tube 12 from the tube voltage V71 to the tube voltage V72. After that, in the time period from the time T72 to the time T73, the tube voltage controlling circuitry 112 supplies the tube voltage V72 to the X-ray tube 12. In this situation, in conjunction with the switching of the tube voltage, the filament controlling circuitry 114 changes the filament(s) that emit electrons to the target 121, by controlling the potential levels of the filament 122a, the filament 122b, and the filament 122c with respect to the intermediate potential Pg71 for each filament.

More specifically, as illustrated in FIG. 11, the filament controlling circuitry 114 maintains the potential of the filament 122b at the potential Pf71. Further, the filament controlling circuitry 114 exercises control so that the potential of the filament 122a is equal to the potential Pf72, which is higher than the intermediate potential Pg71. With these arrangements, the filament controlling circuitry 114 stops the emission of the electrons from the filament 122a to the target 121. Further, the filament controlling circuitry 114 exercises control so that the potential of the filament 122c is equal to the potential Pf71, which is lower than the intermediate potential Pg71. With this arrangement, the filament controlling circuitry 114 causes electrons to be emitted from the filament 122c to the target 121. In other words, by controlling the potential levels of the filaments in conjunction with the switching of the tube voltage at the time T72, the filament controlling circuitry 114 changes the filaments that emit electrons to the target 121 from "the filament 122a and the filament 122b" to "the filament 122b and the filament 122c".

After that, in the time period from the time T72 to the time T73, the filament controlling circuitry 114 causes electrons to be emitted from the filament 122b and the filament 122c to the target 121 and stops the emission of the electrons from the filament 122a to the target 121. With these arrangements, the filament controlling circuitry 114 is able to arrange the tube current in the time period from the time T72 to the time T73 to be equal to the tube current I72 and to also maintain the radiation amount of the X-rays before and after the switching of the tube voltage.

Further, in the time period from the time T72 to the time T73, the X-ray detector 16 detects X-rays having passed through the patient P and having high energy. Further, at the time T73, the X-ray detector 16 reads an electric charge corresponding to the X-ray amount detected in the time period from the time T71 to the time T73 and outputs detection signals to the processing circuitry 20. Further, the image processing function 202 generates a high-energy image on the basis of the difference between the detection signals output at the time T73 and the detection signals output at the time T72. Further, the image processing function 202 performs a discriminating process on the substances contained in the patient P, by using a low-energy image and the high-energy image.

With reference to FIG. 11, the example was explained in which, in conjunction with the switching of the tube voltage, the filaments that emit electrons to the target 121 are changed from "the filament 122a and the filament 122b" to "the filament 122b and the filament 122c"; however, possible embodiments are not limited to this example.

For instance, when electrons were emitted from "the filament 122a" before the switching of the tube voltage, the filament controlling circuitry 114 may switch, in conjunction with the switching of the tube voltage, the filament that emits electrons to the target 121 to "the filament 122b" or to "the filament 122c". Further, when electrons were emitted from "the filament 122a" before the switching of the tube voltage, the filament controlling circuitry 114 may change, in conjunction with the switching of the tube voltage, the filaments that emit electrons to the target 121 to "the filament 122a and the filament 122b", to "the filament 122b and the filament 122c", to "the filament 122a and the filament 122c", or to "the filament 122a, the filament 122b, and the filament 122c".

Further, the filament controlling circuitry 114 is similarly able to change the filament(s) that emit electrons to the target 121 in any of the following situations: When electrons were emitted from "the filament 122b" before the switching of the tube voltage; When electrons were emitted from "the filament 122c" before the switching of the tube voltage; When electrons were emitted from "the filament 122a and the filament 122b" before the switching of the tube voltage; When electrons were emitted from "the filament 122b and the filament 122c" before the switching of the tube voltage; When electrons were emitted from "the filament 122a and the filament 122c" before the switching of the tube voltage; and When electrons were emitted from "the filament 122a, the filament 122b, and the filament 122c" before the switching of the tube voltage.

More specifically, when the X-ray tube 12 includes three filaments, the filament controlling circuitry 114 is able to make any of "42" different changes with respect to the filament(s) that emit electrons to the target 121. Further, when the X-ray tube 12 includes four filaments, the filament controlling circuitry 114 is able to make any of "210" different changes with respect to the filament(s) that emit electrons to the target 121. In other words, when the X-ray tube 12 includes a larger number of filaments, the filament controlling circuitry 114 has a larger number of options as to the filament(s) that emit electrons to the target 121, which makes it possible to easily exercise control over the tube currents.

Further, with reference to FIG. 11, the example was explained in which the tube voltage is switched once while the X-ray tube 12 is radiating the X-ray pulse; however, possible embodiments are not limited to this example. The tube voltage controlling circuitry 112 may switch the tube voltage multiple times while the X-ray tube 12 is radiating an X-ray pulse. In that situation, the filament controlling circuitry 114 is able to change the filament(s) that emit electrons to the target 121, each of the multiple times when the tube voltage is switched.

As an example, a situation will be explained in which tube voltage is switched among tube voltage V81, tube voltage V82 higher than the tube voltage V81, tube voltage V83 higher than the tube voltage V82, and tube voltage V84 higher than the tube voltage V83. In other words, in the present example, a multi-energy acquisition is performed by using four types of X-rays. For example, the filament controlling circuitry 114, at first, applies heat to the filament 122a by using a filament current If81, applies heat to the filament 122b by using a filament current If82, which is larger than the filament current If81, and also applies heat to the filament 122c by using a filament current If83, which is larger than the filament current If82.

Subsequently, the tube voltage controlling circuitry 112 supplies the tube voltage V81 to the X-ray tube 12. In this situation, the filament controlling circuitry 114 causes electrons to be emitted from "the filament 122a, the filament 122b, and the filament 122c" to the target 121. With these arrangements, the filament controlling circuitry 114 arranges the tube current in the X-ray tube 12 to be equal to a tube current I81.

After that, the tube voltage controlling circuitry 112 switches the tube voltage to be supplied to the X-ray tube 12 from the tube voltage V81 to the tube voltage V82. Further, in conjunction with the switching of the tube voltage, the filament controlling circuitry 114 changes the filaments that emit electrons to the target 121 from "the filament 122a, the filament 122b, and the filament 122c" to "the filament 122b and the filament 122c". With these arrangements, the filament controlling circuitry 114 maintains the radiation amount of the X-rays before and after the switching of the tube voltage, by decreasing the tube current in the X-ray tube 12 from the tube current I81 to a tube current I82.

Subsequently, the tube voltage controlling circuitry 112 switches the tube voltage to be supplied to the X-ray tube 12 from the tube voltage V82 to the tube voltage V83. Further, in conjunction with the switching of the tube voltage, the filament controlling circuitry 114 switches the filaments that emit electrons to the target 121 from "the filament 122b and the filament 122c" to "the filament 122a and the filament 122c". With these arrangements, the filament controlling circuitry 114 maintains the radiation amount of the X-rays before and after the switching of the tube voltage, by decreasing the tube current in the X-ray tube 12 from the tube current I82 to a tube current I83.

After that, the tube voltage controlling circuitry 112 switches the tube voltage to be supplied to the X-ray tube 12 from the tube voltage V83 to the tube voltage V84. Further, in conjunction with the switching of the tube voltage, the filament controlling circuitry 114 switches the filaments that emit electrons to the target 121 from "the filament 122a and the filament 122c" to "the filament 122a and the filament 122b". With these arrangements, the filament controlling circuitry 114 maintains the radiation amount of the X-rays before and after the switching of the tube voltage, by decreasing the tube current in the X-ray tube 12 from the tube current I83 to a tube current I84. In other words, when the X-ray tube 12 includes three filaments, the filament controlling circuitry 114 is able to appropriately control the tube currents at the time of the switching of the tube voltage, during the multi-energy acquisition using four types of X-rays.

When the X-ray tube 12 includes three filaments, there are seven options as to the filament(s) that emit electrons to the target 121 as follows: "the filament 122a", "the filament 122b", "the filament 122c", "the filament 122a and the filament 122b", "the filament 122b and the filament 122c", "the filament 122a and the filament 122c", and "the filament 122a, the filament 122b, and the filament 122c". Accordingly, the filament controlling circuitry 114 is able to appropriately control the tube currents at the time of the switching of the tube voltage during the multi-energy acquisition using seven or fewer types of X-rays. Further, when the X-ray tube 12 includes four filaments, the filament controlling circuitry 114 is able to appropriately control the tube currents at the time of the switching of the tube voltage during the multi-energy acquisition using fifteen or fewer types of X-rays. In other words, when the X-ray tube 12 includes a larger number of filaments, the filament controlling circuitry 114 is able to appropriately control the tube currents, in a multi-energy acquisition using a larger number of types of X-rays.

In the first and the second embodiments described above, the example is explained in which the tube voltage is switched at least once while the X-ray tube 12 is radiating the X-ray pulse. In contrast, in a third embodiment, an example will be explained in which the tube voltage is switched for each X-ray pulse radiated by the X-ray tube 12. Some of the constituent elements that have the same configurations as those explained in the first and the second embodiments will be referred to by using the same reference characters as those in FIG. 1 or 4, and the explanations thereof will be omitted.

As an example, a situation will be explained below in which the X-ray tube 12 includes the filament 122a and the filament 122b illustrated in FIG. 4. In other words, the following will describe the example in which the X-ray tube 12 includes the two filaments. Further, in the present embodiment, the X-ray tube 12 includes the grid 123a or the grid 123b. In other words, in the present embodiment, the example will be explained in which the X-ray tube 12 includes a grid used in common by the filament 122a and the filament 122b. Further, in the present embodiment, the example will be explained in which the filament controlling circuitry 114 changes the filament(s) that emit electrons to the target 121, by controlling the potential levels of the plurality of filaments, for each filament.

The tube voltage controlling circuitry 112, at first, sets tube voltage V91 and tube voltage V92 illustrated in FIG. 12. Subsequently, on the basis of the tube voltage V91 and the tube voltage V92, the filament controlling circuitry 114 sets a tube current I91 and a tube current I92. For example, on the basis of the correspondence information R1 in which the sets each made up of a tube voltage level and a tube current value are kept in correspondence with radiation amounts, the filament controlling circuitry 114 sets the tube current I91 and the tube current I92 so that the radiation amount is constant before and after the switching of the tube voltage. FIG. 12 is a chart illustrating an example of a dual-energy acquisition according to a third embodiment.

After that, the filament controlling circuitry 114 sets a filament current (hereinafter "filament current If91") of the filament 122a and a filament current (hereinafter, "filament current If92") of the filament 122b, on the basis of the tube voltage V91 and the tube voltage V92 as well as the tube current I91 and the tube current I92.

For example, on the basis of the correspondence information R2, the filament controlling circuitry 114 sets the filament current If91 so that the current corresponding to the number of electrons generated from the filament 122a at the time of supplying the tube voltage V92 is equal to the tube current I92. Subsequently, on the basis of the filament current If91 and the correspondence information R2, the filament controlling circuitry 114 obtains a tube current I91a corresponding to the number of electrons generated from the filament 122a at the time of supplying the tube voltage V91. After that, the filament controlling circuitry 114 calculates a tube current I91b corresponding to the number of electrons generated from the filament 122b at the time of supplying the tube voltage V91, by subtracting the tube current I91a from the tube current I91. After that, the filament controlling circuitry 114 sets a filament current kept in correspondence with the tube voltage V91 and with the tube current I91b in the correspondence information R2, as the filament current If92.

When an image taking process is to be performed, the filament controlling circuitry 114, at first, applies heat to the filaments by causing the filament current If91 to flow in the filament 122a and causing the filament current If92 to flow in the filament 122b. Further, the grid controlling circuitry 113 sets intermediate potential Pg91 in a position between the filaments 122a and 122b and the target 121.

Subsequently, in the time period from the time T91 to the time T92, the tube voltage controlling circuitry 112 supplies the tube voltage V91 to the X-ray tube 12. In other words, in the time period from the time T91 to the time T92, the tube voltage controlling circuitry 112 causes an X-ray pulse having low energy to be radiated from the X-ray tube 12.

In this situation, the filament controlling circuitry 114 exercises control so that the potential of the filament 122a and the potential of the filament 122b are each equal to potential Pf91, which is lower than the intermediate potential Pg91. With this arrangement, the electrons generated from the filament 122a and the filament 122b are emitted to the target 121, without being blocked by the intermediate potential Pg91. In other words, in the time period from the time T91 to the time T92, the filament controlling circuitry 114 causes the electrons to be emitted from the filament 122a and the filament 122b to the target 121 and arranges the tube current in the X-ray tube 12 to be equal to the tube current I91.

Further, in the time period from the time T91 to the time T92, the X-ray detector 16 detects X-rays having passed through the patient P and having low energy. Further, at the time T92, the X-ray detector 16 reads an electric charge corresponding to the X-ray amount detected in the time period from the time T91 to the time T92 and outputs detection signals to the processing circuitry 20. In the present embodiment, the X-ray detector 16 does not necessarily have to be capable of performing non-destructive reading processes. Further, the image processing function 202 generates a low-energy image on the basis of the detection signals output from the X-ray detector 16.

Further, at the time T92, the tube voltage controlling circuitry 112 stops the supply of the tube voltage to the X-ray tube 12. Also, at the time T93, the tube voltage controlling circuitry 112 starts supplying the tube voltage V92 to the X-ray tube 12. In the time period from the time T93 to the time T94, the tube voltage controlling circuitry 112 supplies the tube voltage V92 to the X-ray tube 12. In other words, in the time period from the time T93 the time to the time T94, the tube voltage controlling circuitry 112 causes an X-ray pulse having high energy to be radiated from the X-ray tube 12. That is to say, in the time period from the time T92 to the time T93, the tube voltage controlling circuitry 112 switches the tube voltage to be supplied to the X-ray tube 12 from the tube voltage V91 to the tube voltage V92.

Further, in conjunction with the switching of the tube voltage, the filament controlling circuitry 114 changes the filament(s) that emit electrons to the target 121, by controlling the potential levels of the filament 122a and the filament 122b with respect to the intermediate potential Pg91 for each filament. For example, as illustrated in FIG. 12, the filament controlling circuitry 114 exercises control so that, in the time period from the time T92 to the time T93, the potential of the filament 122b is equal to potential Pf92, which is higher than the intermediate potential Pg91. With these arrangements, the filament controlling circuitry 114 stops the emission of the electrons from the filament 122b to the target 121.

In other words, by controlling the potential levels of the filaments in conjunction with the switching of the tube voltage, the filament controlling circuitry 114 changes the filament(s) that emit electrons to the target 121 from "the filament 122a and the filament 122b" and to "the filament 122a". With this arrangement, the filament controlling circuitry 114 is able to arrange the tube current in the time period from the time T93 to the time T94 to be equal to the tube current I92 and to also maintain the radiation amount of the X-rays before and after the switching of the tube voltage.

Further, in the time period from the time T93 to the time T94, the X-ray detector 16 detects X-rays having passed through the patient P and having high energy. Further, at the time T94, the X-ray detector 16 reads an electric charge corresponding to the X-ray amount detected in the time period from the time T93 to the time T94 and outputs detection signals to the processing circuitry 20. Also, the image processing function 202 generates a high-energy image on the basis of the detection signals output from the X-ray detector 16. Further, the image processing function 202 performs a discriminating process on the substances contained in the patient P, by using a low-energy image and the high-energy image.

As explained above, even when the tube voltage is switched for each X-ray pulse radiated by the X-ray tube 12, the X-ray diagnostic apparatus 1 according to the third embodiment is able to appropriately control the tube currents. For example, even when the X-ray detector 16 is not capable of performing non-destructive reading processes and it is necessary to switch the tube voltage for each X-ray pulse, the X-ray diagnostic apparatus 1 is able to appropriately control the tube currents.

In FIG. 12, because it does not take much time to change the tube current from the tube current I91 to the tube current I92, the time interval between the time T92 and the time T93 can be short. In other words, the X-ray diagnostic apparatus 1 is able to acquire the low-energy image and the high-energy image in a short period of time and to thereby prevent the positional difference between the images. Consequently, the X-ray diagnostic apparatus 1 makes it possible to perform a discriminating process even on a site having much movement.

Further, with reference to FIG. 12, the example was explained in which the supply of the tube voltage is stopped in the time period from the time T92 to the time T93. In other words, FIG. 12 illustrates the example in which the radiation of the X-ray pulse is controlled by controlling the tube voltage to be supplied to the X-ray tube 12; however, possible embodiments are not limited to this example. For instance, the filament controlling circuitry 114 may control the radiation of the X-ray pulse, by controlling the potential levels of the filament 122a and the filament 122b with respect to the intermediate potential Pg for each filament.

For example, in the time period from the time T91 to the time T92, the tube voltage controlling circuitry 112 supplies the tube voltage V91 to the X-ray tube 12. Also, in the time period from the time T91 to the time T92, the filament controlling circuitry 114 exercises control so that the potential of the filament 122a and the potential of the filament 122b are each equal to the potential Pf91, which is lower than the intermediate potential Pg91. With these arrangements, the filament controlling circuitry 114 causes an X-ray pulse having low energy to be radiated from the X-ray tube 12 in the time period from the time T91 to the time T92.

Further, in the time period from the time T92 to the time T93, the filament controlling circuitry 114 exercises control so that the potential of the filament 122a and the potential of the filament 122b are each equal to the potential Pf92, which is higher than the intermediate potential Pg91. With this arrangement, the filament controlling circuitry 114 stops the radiation of the X-rays from the X-ray tube 12 in the time period from the time T92 to the time T93. Further, in the time period from the time T92 to the time T93, the tube voltage controlling circuitry 112 switches the tube voltage to be supplied to the X-ray tube 12 from the tube voltage V91 to the tube voltage V92.

For example, in the time period from the time T93 to the time T94, the tube voltage controlling circuitry 112 supplies the tube voltage V92 to the X-ray tube 12. Also, in the time period from the time T93 to the time T94, the filament controlling circuitry 114 exercises control so that the potential of the filament 122a is equal to the potential Pf91, and also exercises control so that the potential of the filament 122b is equal to the potential Pf92. With these arrangements, the filament controlling circuitry 114 causes an X-ray pulse having high energy to be radiated from the X-ray tube 12 in the time period from the time T93 to the time T94. Further, the filament controlling circuitry 114 is able to maintain the radiation amount of the X-rays between the X-ray pulse radiated in the time period from the time T91 to the time T92 and the X-ray pulse radiated in the time period from the time T93 to the time T94.

In the X-ray diagnostic apparatus 1 illustrated in FIGS. 1 and 4, the processing functions are stored in the memory 17 in the form of computer-executable programs. The tube voltage controlling circuitry 112, the grid controlling circuitry 113, the filament controlling circuitry 114, and the processing circuitry 20 are processors configured to realize the functions corresponding to the programs by reading and executing the programs from the memory 17. In other words, the circuits that have read the programs have the functions corresponding to the read programs.

FIG. 1 illustrates the example in which the processing functions of the controlling function 201, the image processing function 202, and the display controlling function 203 are realized by the single processing circuit (i.e., the processing circuitry 20); however, possible embodiments are not limited to this example. For instance, the processing circuitry 20 may be structured by combining together a plurality of independent processors, so that the processing functions are realized as a result of the processors executing the programs. In other words, the processing functions of the processing circuitry 20 may be distributed as appropriate among a plurality of processing circuits. Similarly, the processing functions of any of the tube voltage controlling circuitry 112, the grid controlling circuitry 113, and the filament controlling circuitry 114 may be distributed as appropriate among a plurality of processing circuits. Further, the processing functions of the processing circuitry 20, the tube voltage controlling circuitry 112, the grid controlling circuitry 113, and the filament controlling circuitry 114 may be integrated as appropriate into one or more processing circuits.

Further, when any of the tube voltage controlling circuitry 112, the grid controlling circuitry 113, the filament controlling circuitry 114, and the processing circuitry 20 is structured by combining together a plurality of processors, the plurality of processors may be distributed among mutually-different processing devices. In other words, the X-ray diagnostic apparatus 1 may include the plurality of physically-different processing devices.

In one example, the processing circuitry 20 may be structured by combining a first processor configured to realize the controlling function 201 and the display controlling function 203 with a second processor configured to realize the image processing function 202. Further, a first processing device includes the first processor, while a second processing device connected to the first processing device via a network includes the second processor.

In that situation, for example, the controlling function 201 included in the first processing device is configured to acquire detection signals by performing an image taking process on the patient P and to transmit the acquired detection signals to the second processing device via the network. In this situation, the image processing function 202 included in the second processing device is configured to generate X-ray image data based on the detection signals as being triggered by receiving the detection signals and to perform a discriminating process based on the X-ray image data. Further, the image processing function 202 included in the second processing device is configured to transmit a result of the discriminating process to the first processing device via the network. After that, the display controlling function 203 included in the first processing device is configured to cause the display 18 to display the result of the discriminating process.

The abovementioned network may be configured with a local network closed in a facility or may be a network routed through the Internet. In other words, the first processing device and the second processing device described above may be provided in mutually-different facilities. In one example, the first processing device may be provided in a hospital where the patient P is present, whereas the second processing device may be realized with a group of servers (a cloud) connected to the first processing device via the network.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 17.

Further, with reference to FIG. 1, the example was explained in which the single memory (i.e., the memory 17) stores therein the programs corresponding to the processing functions; however, it is also acceptable to provide a plurality of memories 17 in a distributed manner so that each of the circuits is configured to read a corresponding program from one of the individual memories 17. Further, instead of saving the programs in the one or more memories 17, it is also acceptable to directly incorporate the programs in the circuits of the one or more processors. In that situation, the one or more processors realize the functions by reading and executing the programs incorporated in the circuits thereof.

Further, although the X-ray diagnostic apparatus 1 is described in the above embodiments, the present disclosure is also applicable to any other apparatus including the X-ray high-voltage device 11 and the X-ray tube 12. For example, an X-ray Computed Tomography (CT) apparatus may include the X-ray high-voltage device 11 and the X-ray tube 12 described above. For example, the X-ray CT apparatus may be configured to perform the dual-energy acquisition or the multi-energy acquisition by using a fast switching method by which the tube voltage is switched for each X-ray radiation angle with respect to the patient during a CT scan. In this situation, in conjunction with the switching of the tube voltage, the X-ray CT apparatus is configured to change the filament(s) selected from among the plurality of filaments to emit electrons to the target 121, by controlling the potential levels of the plurality of filaments with respect to the intermediate potential Pg for each filament and to thereby appropriately control tube currents. With these arrangements, for example, the X-ray CT apparatus is able to keep the radiation amount of the X-rays constant with respect to each radiation angle or to keep the tube current constant with respect to each radiation angle.

The constituent elements of the apparatuses and the devices described in the embodiments above are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

It is possible to realize the controlling method described in any of the embodiments above by causing a computer such as a personal computer or a workstation to execute a control program prepared in advance. It is possible to distribute the control program via a network such as the Internet. Further, it is also possible to record the control program onto a computer-readable non-transitory recording medium such as a hard disk, a flexible disk (FD), a Compact Disk Read-Only Memory (CD-ROM), a Magneto Optical (MO) disk, a Digital Versatile Disk (DVD), or the like, so as to be executed as being read from the recording medium by a computer.

According to at least one aspect of the embodiments described above, it is possible to appropriately control the tube currents at the time of the switching of the tube voltage.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray tube including a target configured to generate X-rays in response to emission of electrons thereto, a plurality of filaments configured to emit electrons into a substantially same position on the target, and a grid used in common among the plurality of filaments;
intermediate potential setting circuitry configured to set intermediate potential in a position between the plurality of filaments and the target by using the grid; and
filament potential controlling circuitry configured to change one or more filaments selected from among the plurality of filaments to emit the electrons to the target, by controlling potential levels of the plurality of filaments with respect to the intermediate potential for each filament, in conjunction with switching of X-ray tube voltage.

2. The X-ray diagnostic apparatus according to claim 1, wherein the filament potential controlling circuitry either switches among the filaments that emit the electrons to the target or changes a combination of filaments to emit the electrons to the target, by controlling the potential levels of the plurality of filaments for each filament.

3. The X-ray diagnostic apparatus according to claim 1, further comprising:
tube voltage controlling circuitry configured to control the X-ray tube voltage to be supplied to the X-ray tube, wherein
the tube voltage controlling circuitry switches the X-ray tube voltage at least once while the X-ray tube is radiating an X-ray pulse, and
in conjunction with the switching of the X-ray tube voltage, the filament potential controlling circuitry changes the one or more filaments selected from among the plurality of filaments to emit the electrons to the target.

4. The X-ray diagnostic apparatus according to claim 3, further comprising:
an X-ray detector configured to detect the X-rays generated from the X-ray tube and capable of performing a non-destructive reading process; and
processing circuitry configured to process an X-ray image based on a detection result obtained by the X-ray detector, wherein
the X-ray detector performs a first reading process that is non-destructive in response to the switching of the X-ray tube voltage and performs a second reading process later than the switching of the X-ray tube voltage, and
the processing circuitry performs a process related to discriminating substances on a basis of results of the first reading process and the second reading process.

5. The X-ray diagnostic apparatus according to claim 4, wherein the process related to discriminating the substances is a process of generating a plurality of images separated on a basis of a difference in X-ray absorption characteristics.

6. The X-ray diagnostic apparatus according to claim 1, further comprising:
tube voltage controlling circuitry configured to control the X-ray tube voltage to be supplied to the X-ray tube, wherein
the tube voltage controlling circuitry switches the X-ray tube voltage for each of X-ray pulses radiated by the X-ray tube, and
in conjunction with the switching of the X-ray tube voltage, the filament potential controlling circuitry changes the one or more filaments selected from among the plurality of filaments to emit the electrons to the target.

7. The X-ray diagnostic apparatus according to claim 1, wherein the filament potential controlling circuitry causes electrons to be emitted from one or more of the filaments having lower potential than the intermediate potential and stops emission of electrons from one or more of the filaments having higher potential than the intermediate potential, by controlling the potential levels of the plurality of filaments with respect to the intermediate potential for each filament.

8. The X-ray diagnostic apparatus according to claim 1, wherein the filament potential controlling circuitry maintains a radiation amount of the X-rays before and after the switching of the X-ray tube voltage, by changing the one or more filaments selected from among the plurality of filaments to emit the electrons to the target.

9. The X-ray diagnostic apparatus according to claim 8, wherein the filament potential controlling circuitry maintains the radiation amount of the X-rays before and after the switching of the X-ray tube voltage, by setting one or more tube currents for time periods before and after the switching of the X-ray tube voltage to be supplied to the X-ray tube on a basis of correspondence information in which sets each made up of an X-ray tube voltage level and a tube current value are kept in correspondence with radiation amounts and further causing the tube currents set for the time periods before and after the switching of the X-ray tube voltage to flow in the X-ray tube by changing the one or more of the filaments that emit the electrons to the target in conjunction with the switching of the X-ray tube voltage.

10. The X-ray diagnostic apparatus according to claim 1, wherein the filament potential controlling circuitry maintains the tube current in the X-ray tube before and after the switching of the X-ray tube voltage, by changing the one or more filaments selected from among the plurality of filaments to emit the electrons to the target.

11. An X-ray tube comprising:
a target configured to generate X-rays in response to emission of electrons thereto;
a plurality of filaments configured to emit electrons into a substantially same position on the target; and
a grid used in common among the plurality of filaments, wherein,
one or more filaments selected from among the plurality of filaments to emit the electrons to the target are changed by controlling, in conjunction with switching of X-ray tube voltage, potential levels of the filaments with respect to intermediate potential that is set, while using the grid, in a position between the plurality of filaments and the target.

12. An X-ray diagnostic apparatus comprising:
an X-ray tube including a target configured to generate X-rays in response to emission of electrons thereto, a plurality of filaments configured to emit electrons into a substantially same position on the target, and at least one grid; and
changing circuitry configured to change a quantity of filaments selected from among a plurality of filaments to emit electrons to the target by controlling, in conjunction with switching of X-ray tube voltage, one or both of: same or mutually-different levels of intermediate potential set in positions that are between each of the plurality of filaments and the target by using said at least one grid; and potential levels of the plurality of filaments.

\* \* \* \* \*